（12）United States Patent
Khoo et al.

(10) Patent No.: US 12,377,414 B2
(45) Date of Patent: Aug. 5, 2025

(54) MICROFLUIDIC DEVICE AND METHOD FOR DETECTING AN INFECTED CELL IN A FLUID SAMPLE

(71) Applicants: City University of Hong Kong, Kowloon (HK); The Hong Kong Polytechnic University, Kowloon (HK)

(72) Inventors: Bee Luan Khoo, Kowloon (HK); Song Lin Chua, Kowloon (HK); Junchen Liao, Kowloon (HK)

(73) Assignees: City University of Hong Kong, Kowloon (HK); The Hong Kong Polytechnic University, Kowloon (HK)

( * ) Notice: Subject to any disclaimer, the term of this patent is extended or adjusted under 35 U.S.C. 154(b) by 0 days.

(21) Appl. No.: 17/674,087

(22) Filed: Feb. 17, 2022

(65) Prior Publication Data

US 2022/0258160 A1    Aug. 18, 2022

Related U.S. Application Data

(60) Provisional application No. 63/150,716, filed on Feb. 18, 2021.

(51) Int. Cl.
*B01L 3/00*    (2006.01)
*G01N 1/30*    (2006.01)
*G01N 21/64*    (2006.01)

(52) U.S. Cl.
CPC ... *B01L 3/502715* (2013.01); *B01L 3/502753* (2013.01); *G01N 1/30* (2013.01);
(Continued)

(58) Field of Classification Search
CPC ......... B01L 3/502715; B01L 3/502753; B01L 3/502761; B01L 2300/0864; B01L 2400/0463; B01L 2200/0652; B01L 3/502707; B01L 2200/0636; B01L 2300/088; G01N 21/6458; G01N 1/30;
(Continued)

(56) References Cited

U.S. PATENT DOCUMENTS

2012/0315690 A1* 12/2012 Di Carlo ............... G01N 15/10
                                                            209/132
2014/0330244 A1* 11/2014 Hyde ..................... A61B 5/076
                                                            424/278.1

(Continued)

OTHER PUBLICATIONS

Bransky A, Korin N, Nemirovski Y, Dinnar U. Correlation between erythrocytes deformability and size: a study using a microchannel based cell analyzer. Microvasc Res. Jan. 2007;73(1):7-13. doi: 10.1016/j.mvr.2006.09.001. Epub Nov. 22, 2006. PMID: 17123552. (Year: 2006).*

(Continued)

*Primary Examiner* — Elizabeth A Robinson
*Assistant Examiner* — Tingchen Shi
(74) *Attorney, Agent, or Firm* — Renner, Kenner, Greive, Bobak, Taylor & Weber

(57) ABSTRACT

A microfluidic device containing an inlet, a microchannel in fluid communication with the inlet, and a plurality of outlets in fluid communication with the microchannel. The microchannel contains a loop; or from about 1 loop to about 50 loops; or from about 2 loops to about 25 loops; or from about 5 loops to about 15 loops. A method for detecting an infected cell may employ the microfluidic device.

14 Claims, 13 Drawing Sheets

(52) U.S. Cl.
CPC ..... *G01N 21/6428* (2013.01); *G01N 21/6458* (2013.01); *B01L 2300/0864* (2013.01); *B01L 2300/088* (2013.01); *G01N 2021/6439* (2013.01)

(58) Field of Classification Search
CPC ........... G01N 21/6428; G01N 15/1475; G01N 33/569; G01N 15/0255; G01N 2015/0065; G01N 2015/0288; G01N 2015/1493; G01N 2015/008; G01N 2015/149; G01N 2015/0693; G01N 2015/0294; G01N 2015/1495; G01N 2015/1006; G01N 2015/1497; G01N 2015/1486; G01N 2021/6439
See application file for complete search history.

(56) References Cited

U.S. PATENT DOCUMENTS

2016/0303565 A1* 10/2016 Bhagat ............... G01N 15/0255
2018/0136210 A1*  5/2018 Khoo ................ B01L 3/502761

OTHER PUBLICATIONS

Peters, R.P. et al. 2004. 4(12). New developments in the diagnosis of bloodstream infections. The Lancet infectious diseases. pp. 751-760.
Peker, N. et al. 2018. 24(9). Diagnosis of bloodstream infections from positive blood cultures and directly from blood samples: recent developments in molecular approaches. Clin Microbiol Infect. pp. 944-955.
Masters, T.A. et al. 2013. 110(29). Plasma membrane tension orchestrates membrane trafficking, cytoskeletal remodeling, and biochemical signaling during phagocytosis. Proceedings of the National Academy of Sciences. pp. 11875-11880.
Yap, B. et al. 2005. 98(5). Mechanical deformation of neutrophils into narrow channels induces pseudopod projection and changes in biomechanical properties. Journal of Applied Physiology. pp. 1930-1939.
Srivastava, N. et al. 2020. 117(5). Pressure sensing through Piezo channels controls whether cells migrate with blebs or pseudopods. Proceedings of the National Academy of Sciences. pp. 2506-2512.
Buyck, J.M. et al. 2013. 57(5). Pharmacodynamic evaluation of the intracellular activity of antibiotics towards Pseudomonas aeruginosa PAO1 in a model of THP-1 human monocytes. Antimicrob Agents Chemother. pp. 2310-2318.
Garai, P. et al. 2019. 15(6): 1007812. Killing from the inside: Intracellular role of T3SS in the fate of Pseudomonas aeruginosa within macrophages revealed by mgtC and oprF mutants. PLoS Pathog.
Garcia-Medina, R. et al. 2005. 73(12). Pseudomonas aeruginosa Acquires Biofilm-Like Properties within Airway Epithelial Cells. Infection and Immunity. pp. 8298-8305.
Hu, S. et al. 2018. 8(2). Revealing elasticity of largely deformed cells flowing along confining microchannels. RSC advances. pp. 1030-1038.
Bedi, B. et al. 2016. 84(7). Enhanced Clearance of Pseudomonas aeruginosa by Peroxisome Proliferator-Activated Receptor Gamma. Infect Immun. pp. 1975-1985.
Shin, H. et al. 2017. 85(3):e00935-16. Pseudomonas aeruginosa GroEL Stimulates Production of PTX3 by Activating the NF-kappaB Pathway and Simultaneously Downregulating MicroRNA-9. Infect Immun.
Zhou, Y. Z. et al. 2018. 4:5. Sheathless inertial cell focusing and sorting with serial reverse wavy channel structures. Microsyst Nanoeng.
Herrmann, N. et al. 2019. 13. 061501. Spiral microfluidic devices for cell separation and sorting in bioprocesses. Biomicrofluidics.
Chen, C.K. et al. 2020. 10(17). Urine biopsy technologies: Cancer and beyond. Theranostics. pp. 7872-7888.
Khoo, B.L. et al. 2019. 3:30. Liquid biopsy for minimal residual disease detection in leukemia using a portable blast cell biochip. NPJ Precis Oncol.
Lim, E.J. et al. 2014. 5: 4120. Inertio-elastic focusing of bioparticles in microchannels at high throughput. Nat Commun.
Amini, H. et al. 2014. 14(15). Inertial microfluidic physics. Lab on a Chip. pp. 2739-2761.
Guzniczak, E. et al. 2020. 20(3). Deformability-induced lift force in spiral microchannels for cell separation. Lab on a Chip. pp. 614-625.
Gossett, D.R. et al. 2012. 109(20). Hydrodynamic stretching of single cells for large population mechanical phenotyping. Proc Natl Acad Sci U S A. pp. 7630-7635.
Mok, N. et al. 2020. 11(7). Vanillin inhibits PqsR-mediated virulence in Pseudomonas aeruginosa. Food & Function. pp. 6496-6508.
Francis, M.S. et al. 1996. 45(5). Effect of multiplicity of infection on Listeria monocytogenes pathogenicity for HeLa and Caco-2 cell lines. J Med Microbiol. pp. 323-330.
Orsini, J. et al. 2012. 4(6). Microbiological profile of organisms causing bloodstream infection in critically ill patients. Journal of clinical medicine research. pp. 371-377.
Rosales, C. 2018. 9: 113. Neutrophil: a cell with many roles in inflammation or several cell types? Frontiers in physiology.
Dean, L. et al. 2005. vol. 2. Blood groups and red cell antigens. NCBI Bethesda, MD, USA.
Chua, S.L. et al. 2016. 6(11):160162 . Reactive oxygen species drive evolution of pro-biofilm variants in pathogens by modulating cyclic-di-GMP levels. Open Biology.
Mickiewicz, K.M. et al. 2019. 10(1): 4379. Possible role of L-form switching in recurrent urinary tract infection. Nat Commun.
Tuchscherr, L., et al. 2011. 3(3). *Staphylococcus aureus* phenotype switching: an effective bacterial strategy to escape host immune response and establish a chronic infection. EMBO Mol Med. pp. 129-141.
Lee, A. et al. 2007. 45(11). Detection of bloodstream infections in adults: how many blood cultures are needed? J Clin Microbiol. pp. 3546-3548.
Chua, S.L. et al.2016. 7(1): 10750. Selective labelling and eradication of antibiotic-tolerant bacterial populations in Pseudomonas aeruginosa biofilms. Nature communications.
Yang, L. et al.2011. 108(18). Evolutionary dynamics of bacteria in a human host environment. Proceedings of the National Academy of Sciences. pp. 7481-7486.
Chua, S.L. et al. 2014. 5(1): 4462. Dispersed cells represent a distinct stage in the transition from bacterial biofilm to planktonic lifestyles. Nature Communications.
Hu, S., et al. 2016. 12(17). Multiparametric biomechanical and biochemical phenotypic profiling of single cancer cells using an elasticity microcytometer. Small. pp. 2300-2311.
Ren, J., et al. 2020. 20(22). Nondestructive quantification of single-cell nuclear and cytoplasmic mechanical properties based on large whole-cell deformation. Lab on a Chip. pp. 4175-4185.
Chan, S.Y. et al. 2021. 15. Biofilm matrix disrupts nematode motility and predatory behavior. The ISME Journal. pp. 260-269.
Blauwkamp, T.A. et al. 2019. 4(4). Analytical and clinical validation of a microbial cell-free DNA sequencing test for infectious disease. Nature microbiology. pp. 663-674.
Shen, H. et al. 2016. 8(30). Rapid and Selective Detection of Pathogenic Bacteria in Bloodstream Infections with Aptamer-Based Recognition. ACS Appl Mater Interfaces. pp. 19371-19378.
Zhu, Y. et al. 2016. 7(5). Sensitive and fast identification of bacteria in blood samples by immunoaffinity mass spectrometry for quick BSI diagnosis. Chem Sci. pp. 2987-2995.
Conzelmann, C. et al. 2020. 181: 104882. An enzyme-based immunodetection assay to quantify SARS-CoV-2 infection. Antiviral Res.

(56) References Cited

OTHER PUBLICATIONS

Kang, D.K. et al. 2014. 5: 5427. Rapid detection of single bacteria in unprocessed blood using Integrated Comprehensive Droplet Digital Detection. Nat Commun.

* cited by examiner

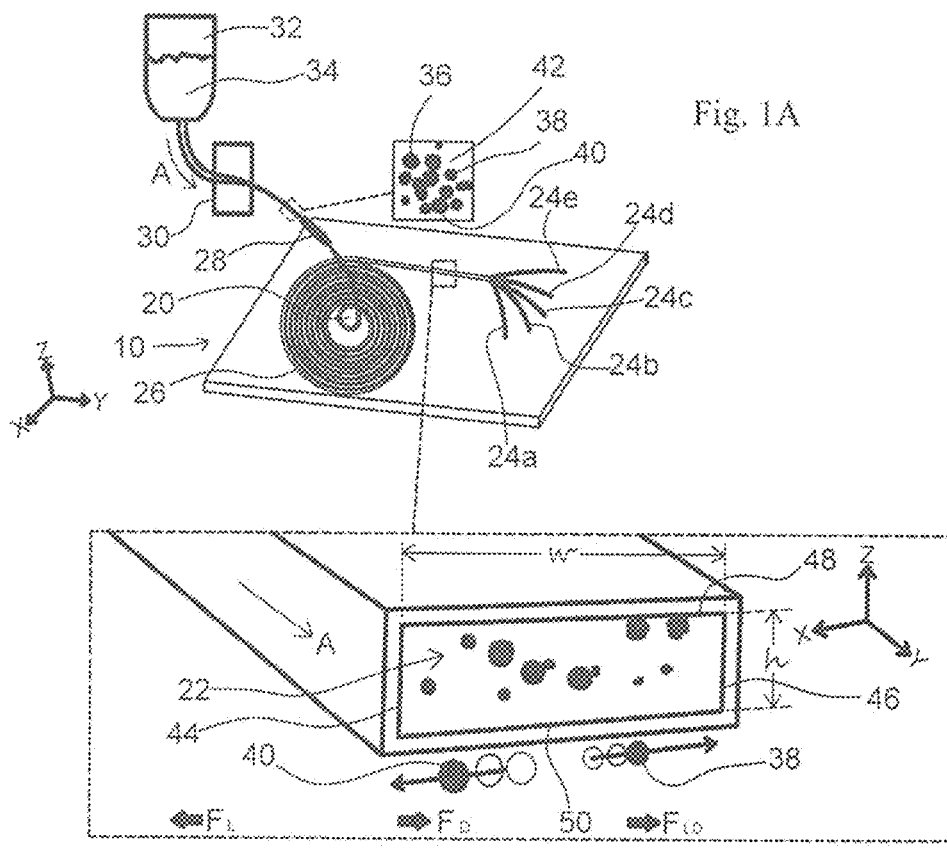
Fig. 1A
Fig. 1B
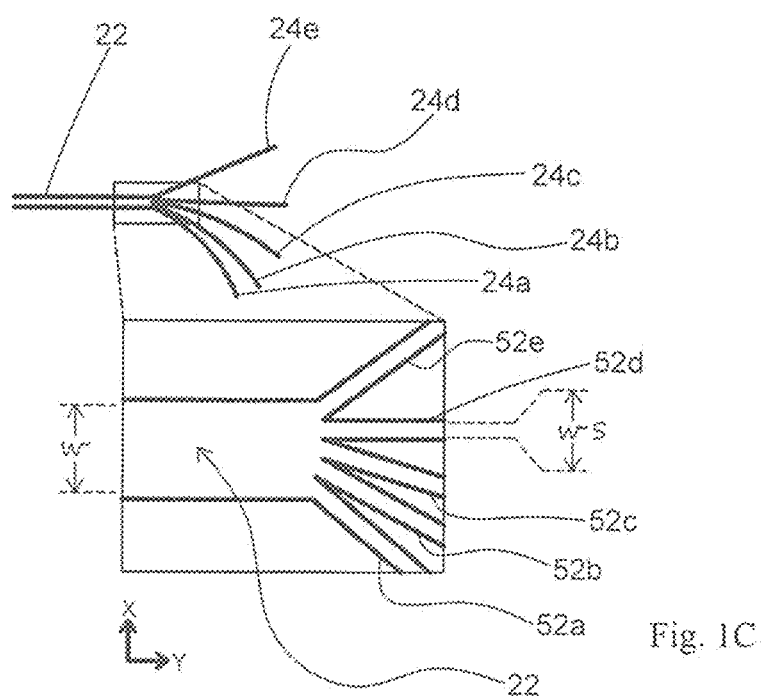
Fig. 1C

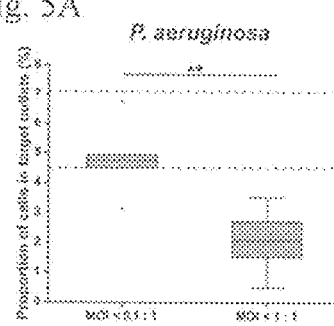
Fig. 5A *P. aeruginosa*
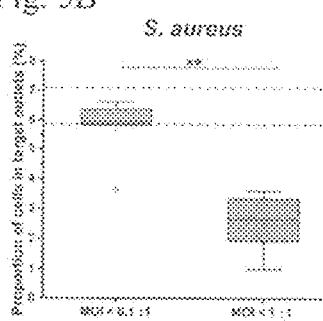
Fig. 5B *S. aureus*
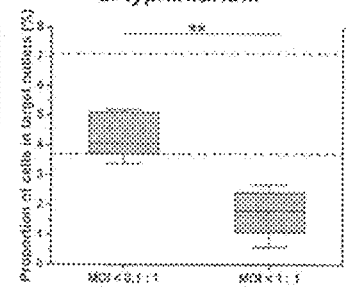
Fig. 5C *S. typhimurium*
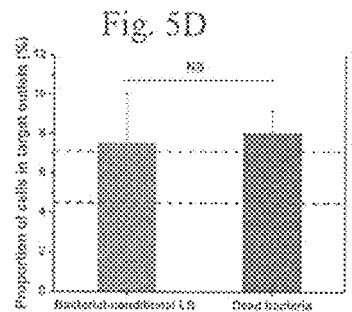
Fig. 5D
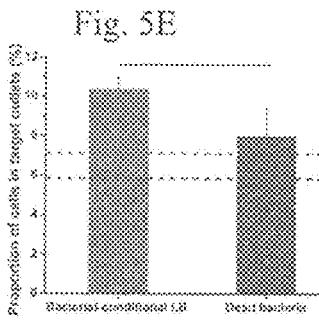
Fig. 5E
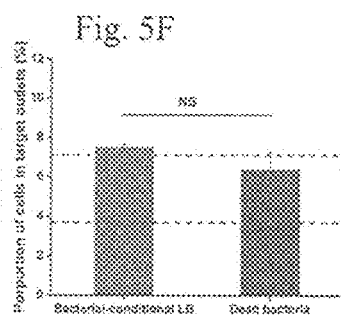
Fig. 5F
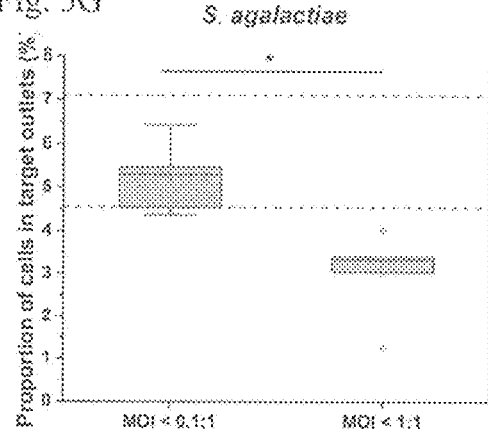
Fig. 5G *S. agalactiae*
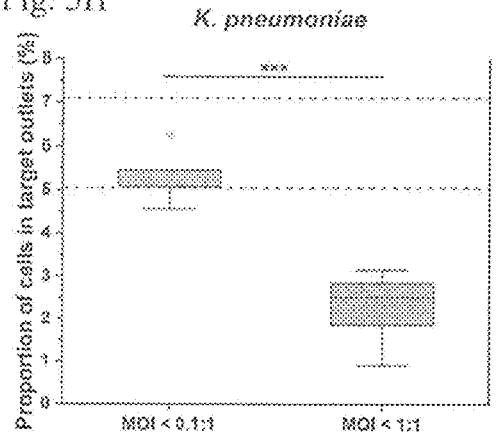
Fig. 5H *K. pneumoniae*

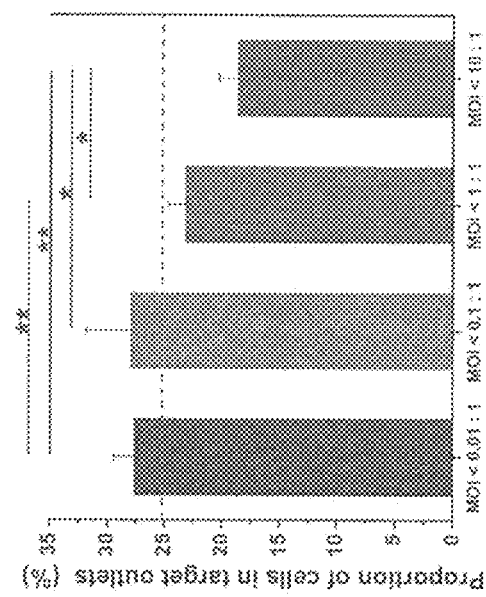
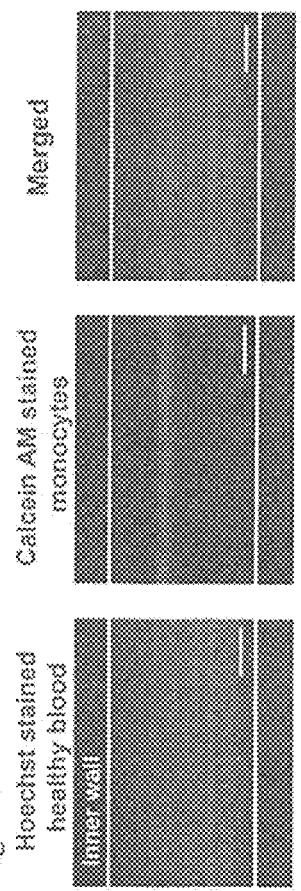
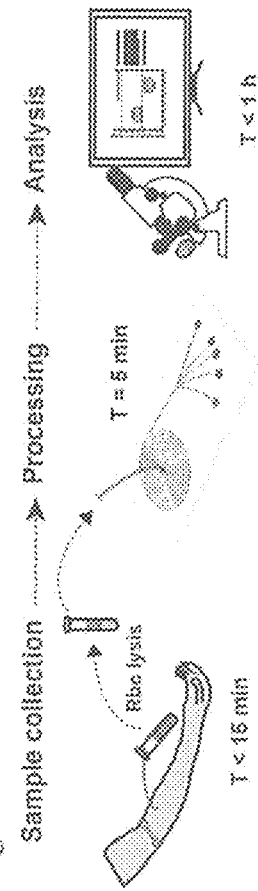
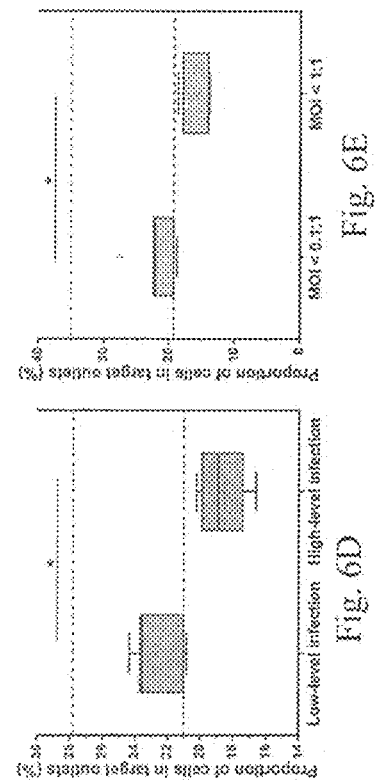
Fig. 6A
Fig. 6B
Fig. 6C
Fig. 6D
Fig. 6E Blood + monocytes at low-level infection Blood + monocytes at high-level infection Blood + monocytes at low-level infection Blood + monocytes at high-level infection

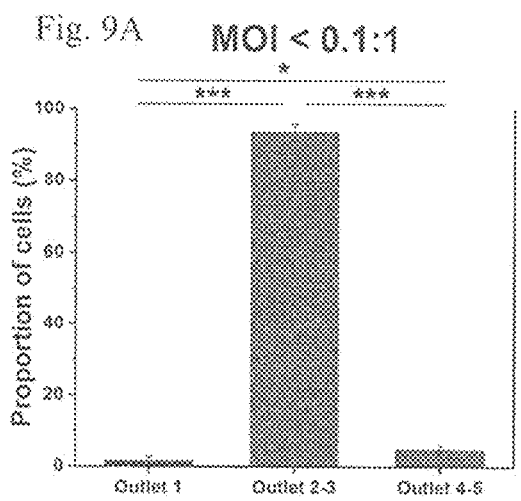
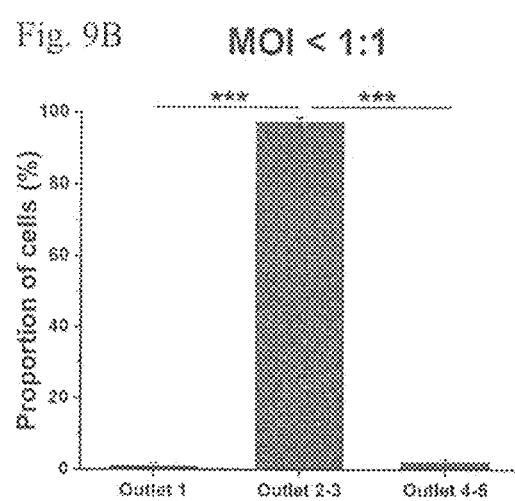
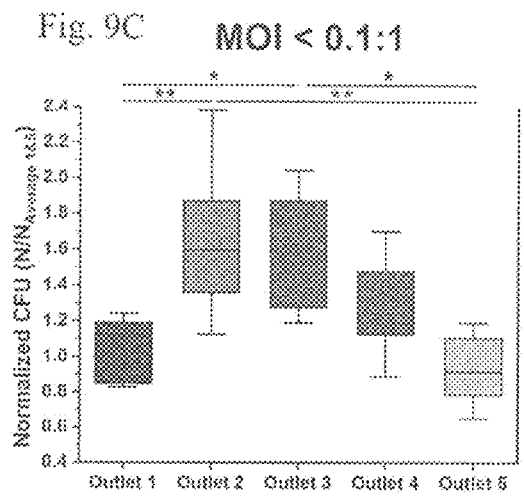
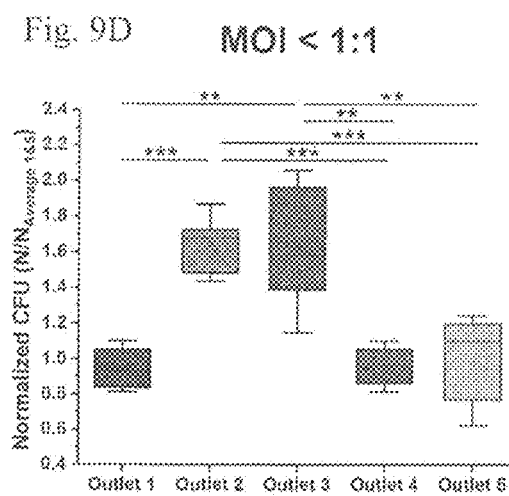

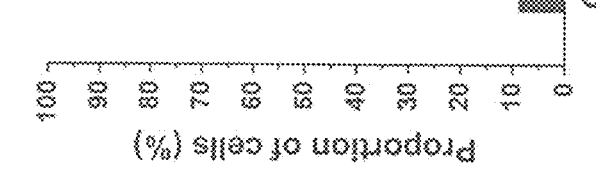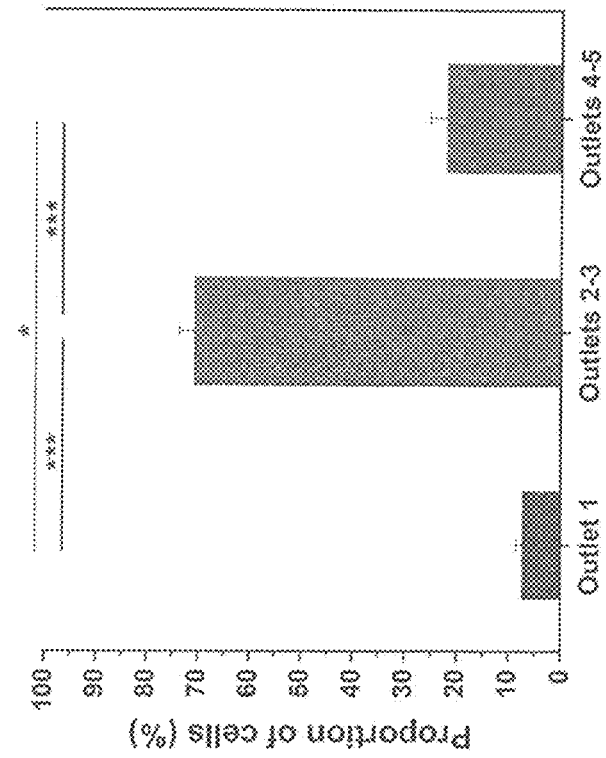

MICROFLUIDIC DEVICE AND METHOD FOR DETECTING AN INFECTED CELL IN A FLUID SAMPLE

FIELD OF THE INVENTION

The present invention relates to a microfluidic device. More specifically, the present invention relates to a microfluidic device for separating cells.

BACKGROUND OF THE INVENTION

It is understood that the rapid detection of pathogens improves clinical results. Current pathogen detection methods include colony culture (>2 days) or genetic sequencing techniques (>24 h), both of which are time-consuming and require complicated, bulky, and expensive equipment as well as very skilled technicians, especially for genetic sequencing and blood cultures.

Phagocytic cells recognize and phagocytose invading microbes for destruction. However, it has been found that bacterial pathogens may remain hidden at low levels from conventional detection methods and/or replicate intracellularly after being phagocytosed by an organism's immune cells. Current phagocytosis-detection approaches involve flow cytometry or a laborious microscopic search for rare bacteria-internalized phagocytes among large populations of uninfected cells. Thus, current detection methods are slow and pose significant challenges in research and clinical settings. Furthermore, some detection assays isolate planktonic bacteria, however these assays are only effective at advanced infection stages.

Many current cell identification assays require radioactive and/or fluorescent labels to indicate which cells are desired and which may be undesired, and to separate various types of cells from a heterogeneous cell population or sample. Such labeling may damage or permanently alter the cell and therefore could destroy or alter information necessary to the researcher or clinician.

Other detection methods rely upon detecting microbes, such as bacteria, in a heterogeneous sample, such as a blood sample, via, for example, bacteria cultures, etc. However, it has been found that bacteria may hide within cells (i.e., intracellular bacteria) and thereby evade recognition by the immune system, leading to false-negative readings in conventional culture assays, the present method provides unique advantages. It is believed that in routine clinical process, clinicians may usually have a narrow treatment window, and any treatment delay may increase the mortality of patients. Besides, while broad-spectrum antibiotic therapy is often currently used to treat most infections, such strategies may not be effective to treat intracellular bacteria. Furthermore, such strategies may actually assist bacteria in developing antibiotic resistance. It is believed that most conventional detection assays, such as the blood culture assays, require from many hours to several days to obtain results.

It is understood in the art that monocytes may phagocytose Gram-negative and Gram-positive bacteria, even at the early stages of infection, so as to protect the body and prevent disease. However, it has been found that some bacteria may survive intracellularly, thereby allowing them to evade immune and clinical detection. Accordingly, attempting to detect free bacteria in such a blood sample, may produce a false negative as the bacteria may be within a cell and thus undetectable using traditional assays.

Spiral microfluidic devices have been used for size-based isolation of circulating tumor cells from blood (see "Ultra-fast, label-free isolation of circulating tumor cells from blood using spiral microfluidics", Warkiani, et al., Nat. Protoc., vol., 11, no. 1, pp. 134-48 (2015 online, 2016)), but Warkani merely uses 1-2 loops, and does not significantly separate infected cells.

There is therefore an urgent need to develop a sensitive, specific, and low-cost method to detect infections early which can be conducted without extensive training and specialized technicians. Accordingly, there remains a need for a label-free, rapid, simple, and cost-effective method to differentiate various cells in a heterogeneous cell population or sample, especially for phagocytic cells. There further remains a need for a method to differentiate infected phagocytes (e.g., those containing bacteria or other microbes therein) from uninfected phagocytes.

BRIEF DESCRIPTION OF THE DRAWINGS

FIG. 1A shows a schematic diagram of an embodiment of the microfluidic device of the present invention;

FIG. 1B shows a close-up, cut-away diagram of a microchannel in the microfluidic device of FIG. 1A;

FIG. 1C shows a close-up schematic view of the microchannel of FIG. 1A, where it splits into sub-channels;

FIG. 5A shows an infection detection graph of *P. aeruginosa;*

FIG. 5B shows an infection detection graph of *S. aureus;*

FIG. 5C shows an infection detection graph of *S. typhimurium;*

FIG. 5D shows the difference between dead and live *P. aeruginosa;*

FIG. 5E shows the difference between dead and live *S. aureus;*

FIG. 5F shows the difference between dead and live *S. typhimurium;*

FIG. 5G show the threshold of uninfected samples of *S. agalactiae;*

FIG. 5H shows the threshold of uninfected samples of *K. pneumoniae;*

FIG. 6A shows a schematic of the clinical validation process;

FIG. 6B shows representative images of Calcein AM stained monocytes and Hoechst stained white blood cells;

FIG. 6C shows the proportion of cells from whole blood samples with spiked monocytes at various infection levels;

FIG. 6D is a graph showing the proportion of cells in the target outlets for uninfected whole blood samples with spiked monocytes at low and high infection rates;

FIG. 6E shows the proportion of cells in target outlets for neutrophil-rich samples from whole blood infected with *P. aeruginosa* at different MOIs.

FIG. 9A shows the outlet distribution of MIMs infected with *P. aeruginosa* for MOI<0.1:1;

FIG. 9B shows the outlet distribution of MIMs infected with *P. aeruginosa* for MOI<1:1;

FIG. 9C shows the distribution in various outlets of MIMs infected with *P. aeruginosa* at MOI<0.1:1;

FIG. 9D shows the distribution in various outlets of MIMs infected with *P. aeruginosa* at MOI<1:1;

FIG. 11A shows the proportion of cells for various outlets for neutrophil-rich samples infected with *P. aeruginosa*;

FIG. 11B shows the proportion of cells for various outlets for neutrophil-rich samples infected with *P. aeruginosa*;

SUMMARY OF THE INVENTION

Figure 1D:
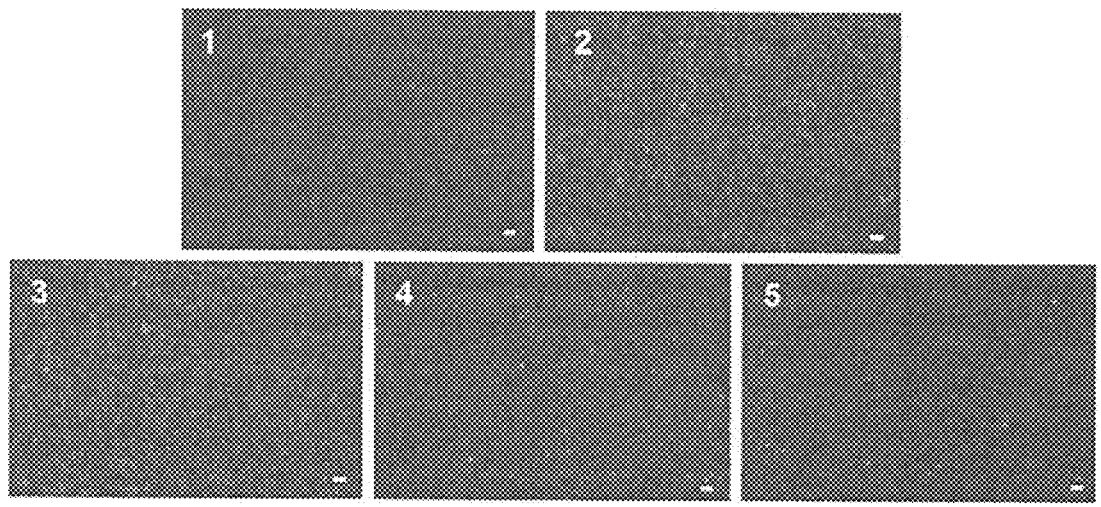
FIG. 1D shows representative images of monocytes collected from the outlets of an embodiment of the microfluidic device of FIG. 1A.

An embodiment of the present invention relates to a microfluidic device containing an inlet, a microchannel in fluid communication with the inlet, and a plurality of outlets in fluid communication with the microchannel. The microchannel contains a loop; or from about 1 loop to about 50 loops; or from about 2 loops to about 25 loops; or from about 5 loops to about 15 loops.

An embodiment of the present invention relates to a method for detecting an infected cell; or an MIM, in a fluid sample comprising the steps of providing a microfluidic device, introducing the fluid sample into the inlet at a predetermined flow rate, collecting the output from an outlet, and quantifying the amount of infected cells in the output.

Without intending to be limited by theory, it is believed that an embodiment of the present invention may provide benefits such as rapid separation of different cells, cost-effective separation of different cells, label-free separation of different cells, simple separation of different cells, etc. It is also believed that an embodiment of the present invention may provide differentiation and segregation of a cell, such as a phagocytic cell, from a heterogeneous cell sample and/or heterogeneous microbe sample. Furthermore, it is believed that the present invention is easy to operate with minimal training, and does not require sophisticated or expensive equipment. It is believed that the methods of the present invention may be easily and accurately conducted by technicians with little training. It is further believed that the present invention may provide high throughput via, for example, multiplexing the device up to, for example, 40 layers. Due to the passive and label-free sorting nature of the present invention, it is believed that many types of immune cells and pathogens may be detected. The invention herein may provide superior results with different cells and heterogeneous cell samples, as compared to existing technology focuses on the detection of planktonic bacteria in circulation. However, patients are often at late stages of systemic infections presented with detected amounts of bacteria in circulation.

It is also believed that the present invention may be applied for both scientific discovery as well as clinical detection purposes. The non-invasive nature of the present invention also ensures that target cells are viable and not damaged after sorting; this permits various forms of downstream processing and analysis.

It is also believed that the present invention may provide early, simple infection diagnosis as the phagocytic immune response to invading microbes is extremely rapid, and may be detected earlier, and/or with lower microbe levels (e.g., viral loads) than other traditional detection methods. In addition, it is believed that the present invention may especially be useful to detect early infection in patients having an immunodeficiency, a high risk of infection, cancer, and other co-morbidities, so as to allow early, more effective, and/or targeted treatment.

The microfluidic device and methods herein may be very cost-effective as they do not require sophisticated equipment, allowing usage within regions with fewer capabilities or within limited budgets.

DESCRIPTION OF THE PREFERRED EMBODIMENTS

Unless otherwise specifically provided, all tests herein are conducted at standard conditions which include a room and testing temperature of 25° C., sea level (1 atm.) pressure, in pH 7 phosphate buffered saline (PBS) solution, and all measurements are made in metric units. Furthermore, all percentages, ratios, etc. herein are by weight, unless specifically indicated otherwise. It is understood that unless otherwise specifically noted, the materials compounds, chemicals, etc. described herein are typically commodity items and/or industry-standard items available from a variety of suppliers worldwide.

As used herein, the term "infected" indicates that a cell, for example a phagocyte, contains a microbe therein, or is bound to a microbe.

As used herein, "inner" with respect to the microchannel refers to the portion closer to the center of the loop. Accordingly the "inner wall" refers to the wall closer to the center of the loop.

As used herein the term "loop" indicates a portion of the microchannel which is routed back to the inlet for reprocessing and simultaneous concentration of sample.

As used herein the term "microbe" indicates a microorganism such as a pathogen; or a bacterium, a fungi, a virus, a parasite, an amoeba, a protozoa, a yeast, and/or a combination thereof. In an embodiment herein the microbe is selected from the group of a pathogen, a parasite and a combination thereof. Such microorganisms are typically seen only under a microscope. The bacterium herein includes various subtypes such as Gram-negative bacteria, Gram-positive bacteria, with an extracellular or intracellular infection modes; or a Gram-negative bacteria.

As used herein a "monocyte with internalized microbe" (MIM) indicates a monocyte which contains a microbe therein.

As used herein, "outer" with respect to the microchannel refers to the portion farther from the center of the loop. Accordingly the "outer wall" refers to the wall farther from the center of the loop.

In an embodiment of the invention herein a microfluidic device contains an inlet, a microchannel in fluid communication with the inlet, and a plurality of outlets in fluid connection with the microchannel. The microchannel contains a loop; or from about 1 loop to about 50 loops; or from about 2 loops to about 25 loops; or from about 5 loops to about 15 loops.

Without intending to be limited by theory it is believed that a microfluidic device may separate and/or detect different cells from a heterogeneous cell sample, such as, monocytes with internalized pathogens (MIMs) from non-MIMs. Based on inertial focusing, the microfluidic device may capitalize on cell physical property differences so as to separate different cells based on the difference in cell stiffness, deformability, cell size, etc. between, for example, bacterial-infected monocytes and white blood cells (WBCs).

Without intending to be limited by theory, it is believed that the present invention may provide early, simple infection diagnosis as the phagocytic immune response to invading microbes is extremely rapid, and may be detected earlier, and/or with lower microbe levels (e.g., viral loads) than other traditional detection methods. In addition, it is believed that the present invention may especially be useful to detect early infection in patients having an immunodeficiency, a high risk of infection, cancer, and other co-morbidities, so as to allow early, more effective, and/or targeted treatment.

Furthermore, without intending to be limited by theory, it is believed that the presence of loops in the microfluidic chamber(s) allows the use of inertial focusing-based microfluidics which helps to concentrate particles of specific sizes by balancing the inertial lift force ($F_L$) and the Dean drag force ($F_D$) in a fully-enclosed system.

To obtain a balance between the inertial and viscous effects experienced within the microfluidic system, the ratio of the inertial force to the viscous force, termed as Reynolds number (Re), should be between 1 to 100 (~1<Re<~100). Re is given by:

$$Re = \frac{\rho UD}{\mu} \quad (1)$$

where $\rho$, U, $\mu$ and D represent the liquid density, flow velocity, viscosity, and hydraulic diameter, respectively.

For a channel with a rectangular cross-section, D=2hw/(h+w) where h and w are the channel cross-section height and width. In inertial focusing-based microfluidics, shear-induced life force and wall-induced life force will make particles migrate across the streamlines. Inertial life force ($F_L$) acting on the particles is the resultant force of the shear-induced life force and wall-induced life force, which is given by:

$$F_L = \frac{\rho C_L U^2 a^4}{D^2} \quad (2)$$

where CL is lift co-efficient, and a is the particle diameter. When fluid flows in curvilinear channels, a centrifugal pressure gradient in the radial direction will drag the particles moving back and forth across the width of channels (see FIG. 3, part A). This drag force, defined as Dean drag force (FD), can be calculated by:

$$F_D = 3\pi U_D a \quad (3)$$

Where $U_D$ is defined as Dean flow (vortices velocity), that can be estimated by:

$$U_D = 1.8 \times 10^{-4} Re \sqrt{\frac{D}{2R}}^{1.63} \quad (4)$$

where R is the radius of channel curvature.

According to Equations (2) and (3), the FL is more dependent on particle diameter than FD (i.e., FL □ a3 and FD □ a). Therefore, only particles larger than specific diameters will experience appreciable FL, which is sufficient to balance the FD and facilitate focusing (see FIG. 3, part B). The threshold diameter for particles to be focused in the system is proportional to the channel dimensions [16, 26] and is estimated by:

$$\frac{a}{D} \geq 0.07 \quad (5)$$

Cell stiffness of the monocytes is quantified by our previously developed elasticity microcytometer [33]. Before the stiffness measuring experiments, the device is coated with 1% (w/w) pluronic F-127 (Sigma-Aldrich, P2443, USA) for 30 min to prevent cell adhesion. The cells are briefly injected with a steady driving pressure into confining microchannels with confining channels. The cells are trapped at a confining channel position where the channel width is narrow enough to trap the cells under the driving pressure. Micrographs of the confining channels with the trapped cells are captured under a phase-contrast inverted microscope (Nikon, Eclipse Ci-L, Japan) at 100 Pa pressure. The cell elasticity is determined by the cell size and position in the confining microchannel obtained from the micrographs. The elastic modulus of monocytes is then calculated based on the hyperelastic Tatara model, as shown in Equation (2):

$$E = \frac{3(1-v^2)A}{2(D_{cell} - W_{deform})}\left(1 + \frac{2Ba^2}{D_{deform}^2}\right)\frac{F_{compress}}{a} - \frac{2A}{\pi(D_{cell} - W_{deform})}\left(1 + \frac{4Ba^2}{5D_{deform}^2}\right)\frac{F_{compress}}{f(a)} \quad (2)$$

Where $D_{cell}$ is the cell diameter, $D_{deform}$ is the deformed cell diameter, $W_{deform}$ is the deformed cell width, v is the Poisson's ratio of a cell, a is the contact radius, and f(a) is the characteristic length of the non-spherical geometry after deformation.

A and B in the above equation can be given as (3), $$A = \frac{(1-\xi)^2}{1-\xi+\frac{\xi^2}{3}}, B = \frac{1-\frac{\xi}{3}}{1-\xi+\frac{\xi^2}{3}}, \xi = 1 - \frac{W_{deform}}{D_{cell}} \quad (3)$$

Where $\xi$ is the deformation of the cell.

In an embodiment herein, the plurality of outlets is from about 2 outlets to about 20 outlets; or from about 2 outlets to about 15 outlets; or from about 3 outlets to about 10 outlets; or about 3 outlets; or about 5 outlets. Without intending to be limited by theory, it is believed that the greater number of outlets, the more tightly the output can be achieved for each particle size; however, it is recognized that a more narrow channel will be more subject to clogging, especially when larger particles/cells are in the heterogeneous sample. Hence, an embodiment herein is a 5-outlet microfluidic chamber. This is designed taking into consideration the smallest dimension of each outlet into account (e.g., the width of each outlet: 500 μm/5=100 μm). Without intending to be limited by theory, it is believed that the greater the number of outlets, the greater the internal resistance which in turn could reduce throughput. In contrast, where the outlets are smaller, it has been found that a smaller number of outlets is more useful because each individual outlet will be larger and therefore less subject to clogging and blockage. In an embodiment herein, the aforementioned problems may be alleviated by widening the main channel in-between the end of the spiral loops and before the outlets split off, so as to allow additional outlets, even for smaller main channel dimensions.

When running heterogeneous samples through the microfluidic device described herein, it has been surprisingly found that infected monocytes are stiffer and are concentrated within the first three outlets of the microfluidic device. Hence, samples with infected monocytes demonstrated lower cell proportions in the target outlets 24d and 24e of FIG. 1A. Using *Pseudomonas aeruginosa* as a proof-of-concept, the limit of detection for bacteria with the microfluidic device herein is 1 bacteria in 100 cells (i.e., a multiplicity of infection (MOI) of 0.01:1). The thresholds of cell proportion within the target outlets (outlets 24d and 24e of FIG. 1A) for non-infected samples and samples of low infection rate (MOI range of from about 0.01:1 to about 0.1:1) are 7.10% and 4.95%, respectively. The optimal monocyte concentration range is about 0.1×10⁶ cells/ml to about 1×10⁶ cells/ml, which corresponds to 1 ml of blood. Results are generated within 1.5 h using only optical imaging. Without intending to be limited by theory, it is believed that the low sample volume requirements and fast processing period allow clinicians and scientists to rapidly screen and identify clinical samples for further evaluation. The platform is widely applied to other pathogens, realizing point of care (POC) assessments for patients infected by potential pathogens.

It is believed that the invention provides an unique diagnostic tool which may be complementary to other existing tools and/or methods to identify cells from within a heterogeneous sample from patients with a higher risk of infection. Furthermore, it is believed that this may be done in a cost-effective manner, allowing rapid phenotyping to be carried out for timely intervention, influencing treatment efficacy and patient survival.

It is believed that the heterogeneous sample may contain a variety of cells, such as, for example, a host cell of animal origin, including a cell selected from the group of a phagocyte, an endothelial cell, an epithelial cells, a tissue cell, and a combination thereof. Furthermore, the cell herein may be infected and thus contain a microbe, therein. Accordingly, the microfluidic device herein may be used for the sorting of cells, including pathogen-infected phagocytes.

Without intending to be limited by theory it is believed that when the microfluidic device contains continuous channels it may induce differential sorting of pathogen-infected phagocytes from non-infected phagocytes through differences in cell deformability.

In an embodiment herein, the microchannel (see FIG. 1C at 22) has a width, w, as measured horizontally (see FIG. 1) between the inner edge (see FIG. 1C at 44) and the outer edge (see FIG. 1C at 46) in the x-axis of FIG. 1C of from about 200 μm to about 800 μm; or from about 300 μm to 700 μm; or from about 400 μm to about 650 μm; or from about 450 μm to about 550 μm as measured in the interior of the microchannel. The microchannel may have a height, h, of from about 50 μm to about 350 μm; or from about 80 μm to about 325 μm; or from about 100 μm to about 310 μm; or from about 130 μm to about 275 μm; or from about 150 μm to about 250 μm, as measured vertically (see FIG. 1) in the z-axis in FIG. 1C between the top edge (see FIG. 1C at 48) and the bottom edge (see FIG. 1C at 50) as measured in the interior of the microchannel. In an embodiment herein, the divergence of the main channel to outlets is placed at about 100 μm; or about 250 μm from the inner wall. Without intending to be limited by theory it is believed that most cells will fit through a microchannel having such dimensions.

In an embodiment herein, the plurality of outlets are connected to the microchannel via a plurality of sub-channels, where the number of sub-channels is the same as the number of outlets. Furthermore, while the height of each sub-channel is typically the same as that of the microchannel, when the width of each sub-channel is added up to form a combined width, then this combined width is typically equivalent to the width of the microchannel. In an embodiment herein, the width of each sub-channel is the same, meaning that the microchannel width is equally-divided to form each of the sub-channel widths. For example, if the width of the microchannel is 500 μm, and there are 5 sub-channels, then each sub-channel has a width of 100 μm.

In an embodiment herein, the width of one or more of the sub-channels, is not equal to the width of another sub-channel. For example, if there are 3 sub-channels and the microchannel is 200 μm in width, then a first sub-channel may be 50 μm in width, a second sub-channel may be 100 μm in width, and a third sub-channel may be 50 μm in width. In another example herein, if there are 4 sub-channels and the microchannel is 375 μm in width, then a first sub-channel may be 50 μm in width, a second sub-channel may be 100 μm in width, a third sub-channel may be 150 μm in width, and a fourth sub-channel may be 75 μm in width.

In an embodiment herein, the distance between the adjacent outlets is from about 100 μm to about 500 μm; or from about 150 μm to about 450 μm; or from about 200 μm to about 400 μm; or from about 250 μm to about 350; or about 250 μm.

An embodiment herein includes a method for detecting an infected cell via the microfluidic device described herein. It is believed that an embodiment herein provides a rapid method for detecting low rates of infection. Furthermore, the microfluidic device herein may be multiplexed for higher throughput processing. Also, the microfluidic device herein may be operated at various flow rates depending on the target cell population, such as a flow rate of about 1.7 ml/min to detect infected monocytes.

In an embodiment herein, the invention includes a label-free detection method of bacterial infection from fluid samples, such as urine, sputum, plasma, blood, etc.; or selected from the group of blood, urine, sputum, lymph fluid, spinal fluid, semen, a tissue extract, and a combination thereof; or where the sputum contains saliva, based on detecting infected cells within a heterogeneous cell population. For example, it is believed that the thresholds of cell proportion within the target outlets (outlets 24d and 24e of FIG. 1A) for non-infected samples and samples of low *Pseudomonas aeruginosa* infection rate (MOI range—0.01:1 to 0.1:1) are 7.10% and 4.95%, respectively.

It is understood in the art that monocytes may phagocytose Gram-negative and Gram-positive bacteria, even at the early stages of infection, so as to protect the body and prevent disease. However, it has been found that some bacteria may survive intracellularly, thereby allowing them to evade immune and clinical detection. However, to this date diagnostic methods have not been developed specifically to exploit this phenomenon and to detect the presence of either early or intracellular infection, mainly due to the technical difficulties of differentiating infected monocytes from other white blood cells (WBCs).

The present invention provides a sensitive, specific, and low-cost method for rapid detection of infection at an early stage, and the microfluidic device may detect monocytes infected with bacteria.

Turning to the figures, FIG. 1A shows a schematic diagram of an embodiment of the microfluidic device, 10, of the present invention. The microfluidic device, 10, contains a single inlet, 20, a microchannel, 22, and a plurality of outlets, 24, in this case 5 outlets, 24a, 24b, 24c, 24d, and 24e. The microchannel, 22, is in fluid communication with the inlet, 20, and the plurality of outlets, 24a, 24b, 24c, 24d, 24e, are in fluid communication with the microchannel, 22. The microchannel contains 10 loops, 26, which form a curvilinear microchannel, 22. The inlet, 20, is sequentially connected to a tube, 28, a pump, 30, and a reservoir, 32. In an embodiment herein, the pump is a syringe pump, a peristaltic pump, a pressure pump, and a combination thereof or a syringe pump, a peristaltic pump, a pressure pump, and a combination thereof or a syringe pump, a pressure pump, and a combination thereof.

The reservoir, 32, may be any reservoir useful to contain a heterogeneous sample, 34, which contains a plurality of red blood cells, 36, monocytes, 38, monocytes with an internalized microbe (MIMs), 40, and microbes, 42, such as bacteria. Typically for blood samples, nucleated cell fractions are processed after blood cell lysis. In an embodiment herein, the monocyte is a monocyte with an internalized microbe; or pathogen.

In an embodiment herein, the microfluidic device contains one inlet and a plurality of outlets; or from about 2 outlets to about 20 outlets; or from about 2 outlets to about 15 outlets; or from about 3 outlets to about 10 outlets; or wherein the plurality of outlets consists of 5 outlets. Without intending to be limited by theory it is believed that such a microfluidic device may provide improved separation while still being easy to manufacture.

In an embodiment herein, the microchannel is arranged such that the inlet is positioned at the center and wherein the loop surrounds the inlet, such as when the loops concentrically surround the inlet. In an embodiment herein, the microchannel branches to form the plurality of outlet. In an embodiment herein, the microchannel is a curvilinear microchannel.

The microfluidic device in FIG. 1A is fabricated based on the standardized soft lithography method, as described in "Ultra-fast, label-free isolation of circulating tumor cells from blood using spiral microfluidics", Warkiani, et al., Nat. Protoc., vol., 11, no. 1, pp. 134-48 (2015 online, 2016), and only requires a small sample volume for detection.

In an embodiment herein, the microfluidic device is fabricated with a mold. The mold is fabricated by photolithography. An aluminum mold is micromachined and mold patterns are replicated with polydimethylsiloxane (PDMS) base (SYLGARD™ 184 Silicone Elastomer kit, Dow, Inc., Germany) by mixing the polymer with the curing agent at a ratio of 10:1. The PDMS is cured in a degassed oven at about 60° C. for about 2 h. After curing, the PDMS layer is gently peeled off from the aluminum mold. A 5 min plasma treatment bonds the PDMS layers, and the device is assembled in the oven at 80° C. for another 2 h.

In an embodiment herein, at least a portion of the microfluidic device produced by a method comprising lithography, 3D printing, and a combination thereof; or lithography.

The microchannel width of the microfluidic device is 500 µm, and the height is 200 µm at the inner and outer walls of the microchannel, respectively. The width of each of the five outlets is 100 µm. The length of the main straight channel is 15 mm, while the length for each of the outlets is 10 mm.

In an embodiment herein, the microchannel contains from about 1 loop to about 50 loops; or from about 2 loops to about 25 loops; or from about 5 loops to about 15 loops. In an embodiment herein the microchannel contains about 10 loops. In an embodiment herein, the loops are a single, concentric spiral loop.

For the cell deformability device, a silicon wafer is coated with protective photoresist AZ5214 (AZ Electronic Materials, Wiesbaden, Germany), followed by UV exposure. The developed silicon wafer with photoresist is then etched by deep reactive-ion etching (DRIE). After removing the protective photoresist using acetone, the etched silicon wafer is treated with silane (Sigma-Aldrich, St. Louis, MO).

The cell separation process with the microfluidic device is based on the principle of inertial focusing. The particles in the microchannel are subjected to two main forces: inertial lift force ($F_L$) and Dean drag force ($F_D$). During device processing, cells are focused as tightly ordered streams when $F_L$ is balanced with $F_D$. Compared with smaller cells, larger cells encounter a larger $F_L$ to balance $F_D$, and these larger cells are driven closer to the inner channel wall. Furthermore, deformable cells would experience an additional lift force ($F_{LD}$), pushing these deformable cells closer to the outer wall. Therefore, as particles with different sizes and deformability experienced various degrees of $F_L$ at different lateral positions of the channel cross-section, differential focusing of the cells occurs, resulting in efficient separation at target outlets.

Without intending to be limited by theory it has surprisingly been found that MIMs, such as monocytes which have engulfed bacteria, are stiffer and/or larger than normal monocytes. Accordingly, it has been further found that such MIMs tend to migrate to the outlets corresponding to, for example, outlet 24b and 24c in FIG. 1. This is believed to be because normal monocytes are more deformable and experience an additional lift force that moves them towards the outer wall, while stiffer and larger MIMs move closer towards the inner wall.

FIG. 1B shows a close-up, cut-away diagram of a microchannel, 22, in the microfluidic device of FIG. 1A. This illustrates the force distribution within a microchannel, 22, where the inertial life force, $F_D$, overall pushes the stiffer and larger MIMs, 40, towards the inner edge, 44, of the microchannel, 22, while the Dean drag force, $F_D$, and the additional lift force, $F_{LD}$, pushes the uninfected, deformable (i.e., less-stiff), regular monocytes, 38, towards the outer edge, 46, of the microchannel, 22.

FIG. 1B also shows a schematic diagram of the microchannel, 22, of the microfluidic device of FIG. 1A also shows that the microchannel, 22, has a width, w, as measured from the inner edge, 44, to the outer edge, 46 which in FIG. 1C corresponds to the z-axis in the interior of the microchannel. The microchannel, 22, also has a height, h, measured from the top edge, 48, to the bottom edge, 50 which in FIG. 1C corresponds to the z-axis in the interior of the microchannel. The heights and widths of the sub-channels is measured along similar axes.

FIG. 1C shows a close-up schematic view of the microchannel, 22, of FIG. 1A, where it splits into sub-channels, 52a, 52b, 52c, 52d, and 52e which lead respectively to outlets 24a, 24b, 24c, 24d, and 24e. In FIG. 1D, the width of each sub-channel, 52, is the sub-channel width, ws, is the same and with 5 sub-channels, 52a, 52b, 52c, 52d, 52e, each sub-channel width, ws is one-fifth of the width, w, of the microchannel, 22. In FIG. 1D it can also be seen that each sub-channel, 52a, 52b, 52c, 52d, 52e, branches off from the microchannel, 22, at substantially the same point along the microchannel, 22. In an embodiment herein each sub-channel does not branch off from the microchannel at substantially the same point along the microchannel.

FIG. 1D shows representative images of monocytes collected from the outlets of an embodiment of the microfluidic device of FIG. 1A. In FIG. 1B, image 1 shows the sample received from outlet 24a, image 2 shows the sample received from outlet 24b, image 3 shows the sample received from outlet 24c, image 4 shows the sample received from outlet 24d, and image 5 shows the sample received from outlet 24e. FIG. 1B shows that most cells are collected from outlets 24b (image 2) and 24c (image 3), and a lower proportion of cells are collected from target outlets 24a (image 1), 24d (image 4) and 24e (image 5). The scale bar in the lower right hand corner of images 1-5 is 50 µm.

Characterization of the Microfluidic Device for Detection of MIMs

Through experimentation with the microfluidic device, cell populations determined a robust cell proportion threshold for uninfected monocyte samples in the target outlets (outlets 24d and 24e of FIG. 1A). In the device, cells are focused as tightly ordered streams where $F_L$ balances with $F_D$. Various cell concentrations between $0.01 \times 10^6$ cells/ml to $2 \times 10^6$ cells/ml are re-stained with Calcein-AM (available worldwide from Thermo-Fisher Scientific) and then tested in the microfluidic device herein and the time-lapsed observations of their focused streams in the microfluidic device recorded.

Figure 2A:
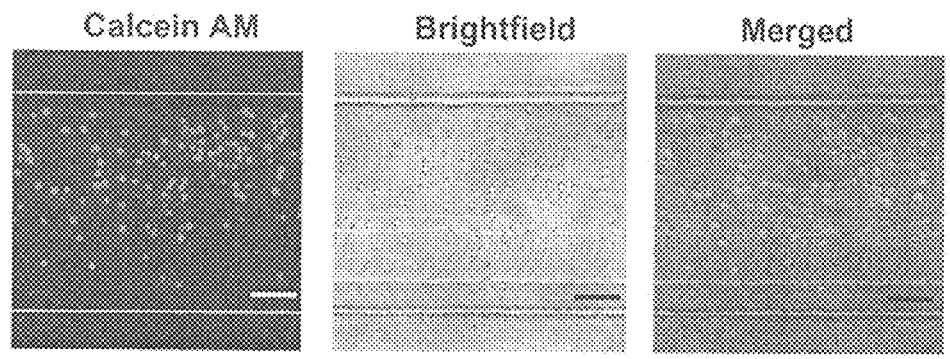
FIG. 2A shows that Calcein-AM-stained monocytes in a main straight channel under stationary conditions are focused into a tightly ordered stream.

FIG. 2A shows that Calcein-AM-stained monocytes in a main straight channel under stationary conditions are focused into a tightly ordered stream. In FIG. 2A, the scale bar=100 µm.

Figure 2B:
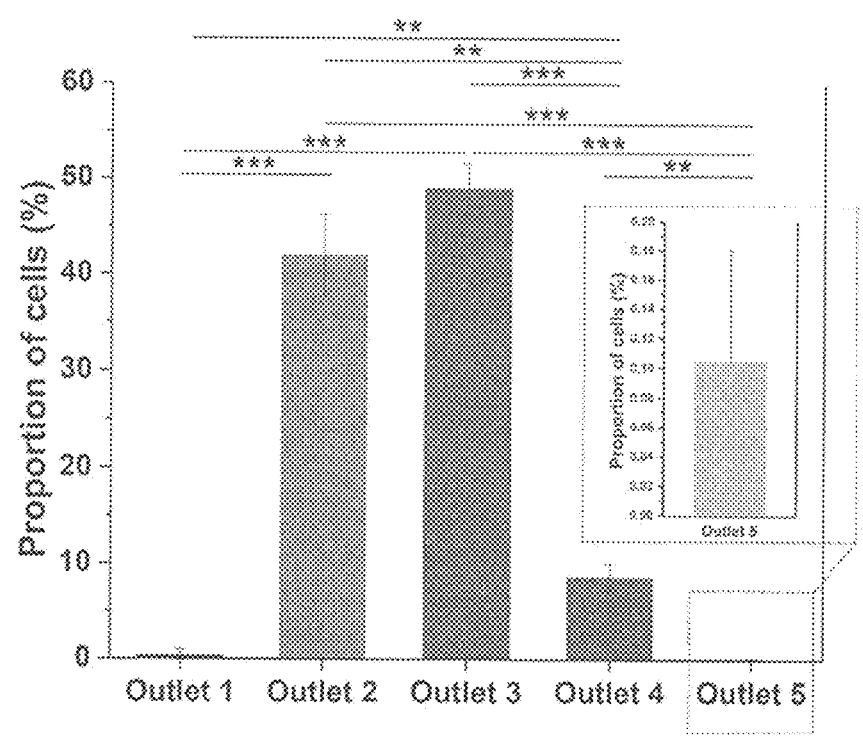
FIG. 2B shows the proportion of cells recovered from each outlet after sorting in the microfluidic device herein.

FIG. 2B shows the proportion of cells recovered from each outlet after sorting in the microfluidic device (see FIG. 1A, at 10), where outlet 1=outlet 24a in FIG. 1A, outlet 2=outlet 24b in FIG. 1A, outlet 3=outlet 24c in FIG. 1A, outlet 4=outlet 24d in FIG. 1A, and outlet 5=outlet 24e in FIG. 1A. In FIG. 2B, * states for p values of <0.01,  states for p values of <0.001, * states for p values of <0.0001.

The Reynolds number affects particle sorting efficiency, which can be influenced by the flow velocity. As the flow rate increases, the focused bandwidth and equilibrium position of cells is affected. Specifically, at a lower flow rate (<1.7 ml/min), the focused bandwidth in the channel cross-section is more diffuse (1.3 ml/min: 101.53±2.39 µm, 1.5 ml/min: 57.52±1.31 µm), while at flow rates higher than 1.7 ml/min, the equilibrium position of the focused streams of cells fluctuates and shifts closer to the inner wall of the device channel. However, it is found that the bandwidth of cells at 1.7 ml/min is consistently focused within 25.5±0.90 µm. Therefore, in an embodiment herein, the predetermined flow rate of the sample through the microfluidic device is from about 1.3 ml/min to about 2.1 ml/min; or from about 1.5 ml/min to about 1.9 ml/min; or about 1.7 ml/min. Without intending to be limited by theory, it is believed that such a flow rate helps to ensure consistency in cell focusing and separation.

Figure 3A:
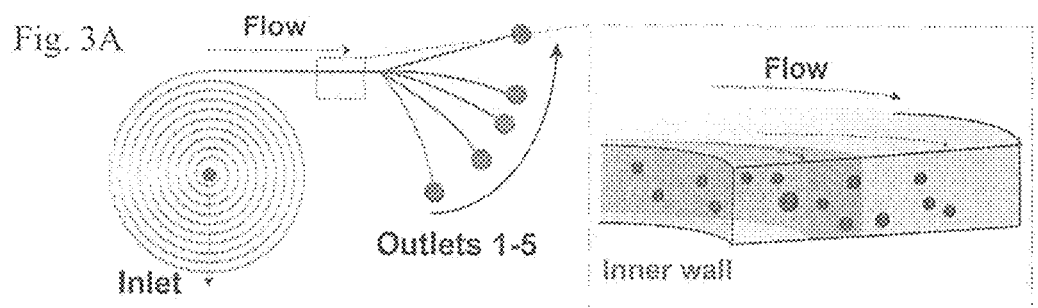
FIG. 3A shows a schematic representation of the optimization setup where the 5 outlets correspond to those shown in FIG. 1A.

FIG. 3A shows a schematic representation of the optimization setup where the 5 outlets correspond to those shown in FIG. 1A.

Figure 3B:
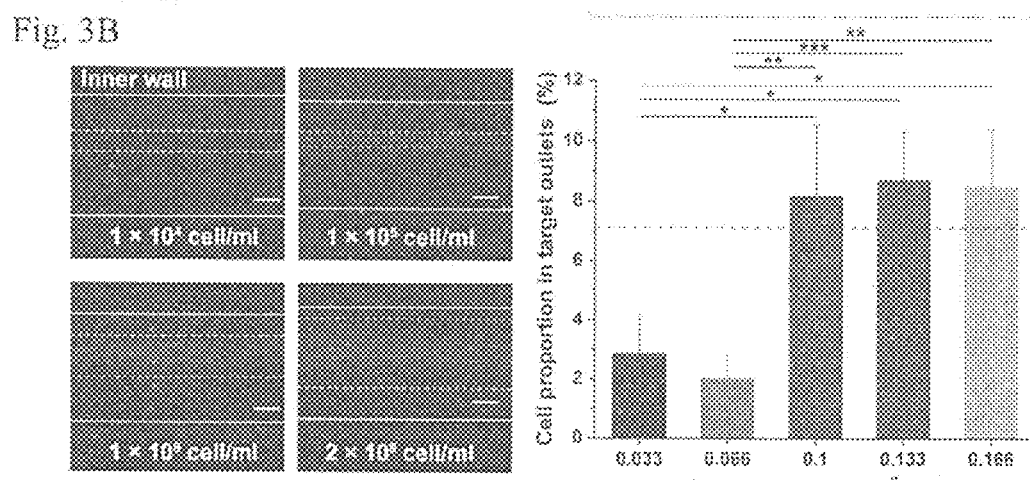
FIG. 3B shows representative images of the monocyte bandwidth at different monocyte concentrations.

FIG. 3B shows representative images of the monocyte bandwidth at different monocyte concentrations. It has also been found that as the cell concentration increases, the focused bandwidth of cells across the channel cross-section widens. The white dotted lines denote the focused bandwidths of the cells. Specifically, it is found that samples with a cell concentration higher than $1 \times 10^6$ cells/ml result in diffused bandwidths of >80 µm, which is larger than the minimum feature size of the microfluidic device, thereby affecting sorting efficiency. The scale bar=100 µm.

Figure 3C:
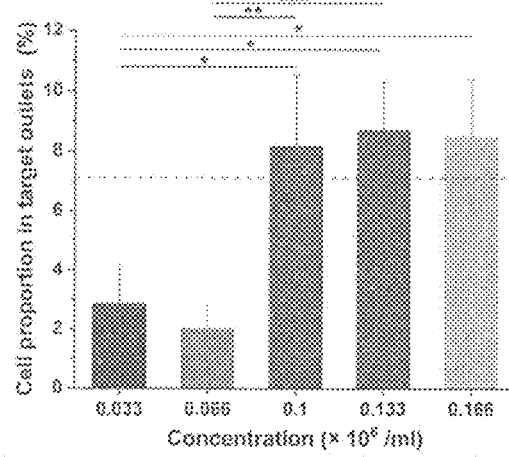
FIG. 3C shows a graph indicating the proportion of cells in target outlets 24d and 24e according to FIG. 1A at different monocyte concentrations.
Figure 3D:
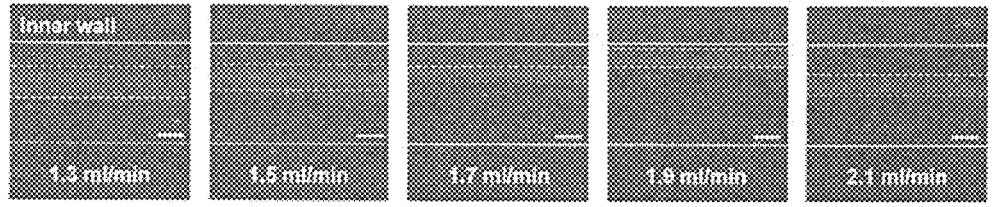
FIG. 3D shows representative images of Calcein-AM-stained monocytes under different flow rates.

FIG. 3C shows a graph indicating the proportion of cells in target outlets (24d and 24e according to FIG. 1A) at different monocyte concentrations. The resultant proportion of cells in the target outlets for samples with a cell concentration range of $0.1 \times 10^6$ cells/ml to $0.166 \times 10^6$ cells/ml is consistently higher (8.17-8.71%), while the resultant proportion of cells in the target outlets for samples with a cell concentration below $0.1 \times 10^6$ cells/ml is negligible (2.0-2.86%). Therefore, the optimal cell concentration range for subsequent runs of the microfluidic device is $0.1 \times 10^6$ cells/ml to $1 \times 10^6$ cells/ml. The threshold for the proportion of cells in the target outlets of uninfected samples within the optimal range of cell concentration is 7.1%, as determined by the value at the 25 percentile. In FIG. 3C, * states for p values of <0.01,  states for p values of <0.001, * states for p values of <0.0001.

FIG. D shows representative images of Calcein-AM-stained monocytes under different flow rates of 1.3 ml/min, 1.5 ml/min, 1.7 ml/min, 1.9 m/min, and 2.1 ml/min). The scale bar=100 µm, indicating that flow rates of ≥1.7 ml/min lead to more focused streams within the microchannel.

In the absence of bacterial infection, it is believed that uninfected monocytes are of a similar size range (15.51±3.25 µm). As such, uninfected monocytes are more evenly distributed across the outlets, albeit more cells are concentrated in outlets 24b and 24c (according to FIG. 1A) due to a higher flow velocity. The proportion of uninfected monocytes in the target outlets for samples with various cell concentrations under $1 \times 10^6$ cells/ml.

Figure 4:
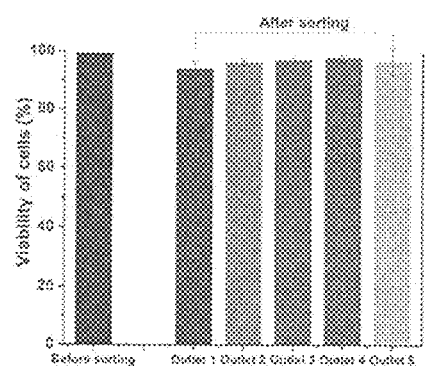
FIG. 4 shows a graph of monocyte viability before and after passage though the microfluidic device herein.

FIG. 4 shows a graph of monocyte viability before and after passage though the microfluidic device herein. Without intending to be limited by theory it is believed that the transient passage of cells through the microfluidic device causes negligible shear stress to the cells during the sorting process. Using Calcein-AM live stains, it can be seen in FIG. 4 that there is no significant difference in monocyte viability before and after sorting. Furthermore, the cell morphology is also largely well conserved, implying that cells' shear stress during processing is negligible and did not result in physical alterations to the cells.

The microfluidic device is validated for early and label-free detection of infection based on the presence of MIMs. An infection modes is established with Pseudomonas aeruginosa (P. aeruginosa), a bacterium commonly found in nature (soil and water bodies) and most human-made environments. However, P. aeruginosa is an opportunistic pathogen to immunocompromised individuals such as the elderly and HIV patients. P. aeruginosa may infect the pulmonary tract, urinary tract, burns and wounds, and is one of the key factors leading to sepsis. Modified P. aeruginosa constitutively producing a green fluorescence protein (GFP) to confirm the presence of infection and validate the MOI.

FIGS. 5A-5H show graphs of infection detection based on the proportion of cells in the target outlets 24d and 24e of FIG. 1A.

Specifically, FIG. 5A, FIG. 5B, and FIG. 5C show the comparable portion of cells in target outlets 24d and 24e of FIG. 1A for P. aeruginosa (4.5%; p value 0.000695), S. aureus (5.85%; p value 0.00072), and S. typhimurium (3.7%; p value 0.001317) at MOI of <0.1:1 and MOI<1:1. These figures also show that the thresholds for uninfected samples is about 7.1% for samples infected at a MOI of <0.1:1.

FIG. 5D, FIG. 5E and FIG. 5F, show that the differences between dead and live P. aeruginosa, S. aureus, and S. typhimurium, respectively, are negligible, based on the proportion of cells in the target outlets 24d and 24e of FIG. 1A.

FIG. 5G and FIG. 5H, show the thresholds (7.1%) of uninfected samples of S. agalactiae (4.54%; p value of 0.002526) and K. pneumoniae (5.05%; p value of 0.0000053), respectively at a MOI<0.1:1. As used in FIGS. 5A-5H, NS=not significant, * states for p values of <0.01,  states for p values of <0.001, and * states for p-values of <0.0001.

It is believed that cell deformability played another key role in the enrichment of infected monocytes, the inventors evaluated the cell stiffness of infected and uninfected monocytes using a deformability assay as described in "Revealing elasticity of largely deformed cells flowing along confining microchannels", Hu, et al., RSC Adv., vol. 8, is. 2, pp. 1030-38 (2018). In order to simulate early-stage and late-stage infections, a range of MOI (0.1:1 to 50:1) is utilized finding that MIMs are significantly stiffer than uninfected monocytes. Interestingly, the stiffness of cells infected at a higher MOI (between 0.1:1 to 1:1) is significantly higher than that of cells infected at a lower MOI (between 0.01:1 to 0.1:1), suggesting that more-infected MIMs are stiffer than less-infected MIMs. However, even the less-infected MIMs from the onset of infection are still sufficient to induce efficient separation and detection with the microfluidic device.

FIG. 6 A, shows a schematic of the clinical validation process where a blood sample and patient-derived clinical isolates are collected from an infected individual and the red blood cells are lysed within 15 minutes. In 5 minutes the sample is processed by being placed into the microfluidic device herein. Finally, within 1 hour, the analysis is performed.

FIG. 6B, shows representative images of Calcein AM stained monocytes and Hoechst stained (healthy) white blood cells in clinical samples where the white scale bar indicates 100 μm.

FIG. 6C, shows the proportion of cells from whole blood samples with spiked monocytes infected at MOI=0.01:1, MOI=0.01:1, MOI=1:1, and MOI=10:1. The dotted line at 25.21% indicates the proportion of uninfected samples.

FIG. 6D, is a graph showing the proportion of cells in the target outlets 24d and 24e of FIG. 1A. for uninfected whole blood samples with spiked monocytes at low infection and high infection rates. The thresholds for samples of low infection rates (27.81%) and high infection rates (21.00%) were denoted by the dotted lines.

FIG. 6E shows the proportion of cells in target outlets 24d and 24e of FIG. 1A for neutrophil-rich samples from whole blood infected at MOI<0.1:1 and <1:1 with P. aeruginosa. The thresholds for uninfected healthy blood samples (34.96%) and neutrophil-rich samples infected at MOI<0.1:1 (19.22%) were denoted by the dotted lines. The proportion of cells in target outlets 24d and 24e of FIG. 1A for samples infected at MOI<0.1:1 and <1:1 with F) CF173-2005 (p-value: 0.000983) and G) CF273-2002 (p-value: 0.000371). The thresholds of uninfected samples (7.10%) and samples infected at MOI<0.1:1 (CF173-2005: 4.40%, CF273-2002: 5.18%) were denoted by the dotted red and blue lines, respectively. In FIGS. 6C-6E, * states for p values of <0.01, ** states for p values of <0.001.

FIGS. 7A-7D show graphs of normalized CFU data for each of 5 microfluidic device outlets. In FIGS. 7A-7D, outlet 1=outlet 24a in FIG. 1A, outlet 2=outlet 24b, outlet 3=outlet 24c in FIG. 1A, outlet 4=outlet 24d in FIG. 1A, and outlet 5=outlet 24e in FIG. 1A. In FIG. 7,  states for p values of <0.001, * states for p values of <0.0001.

Figure 7A:
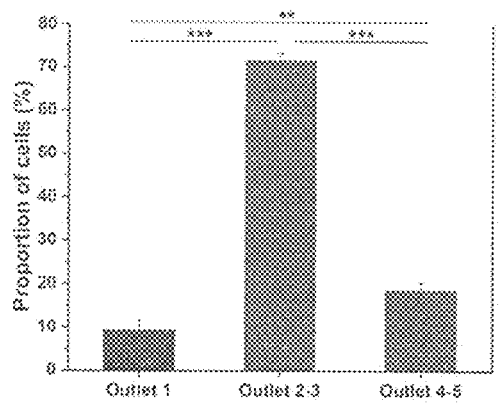
FIG. 7A is a graph showing normalized CFU data for a low-level infection.

FIG. 7A is a graph showing the proportion of cells in various outlets of the microfluidic device in FIG. 1A for a low-level infection.

Figure 7B:
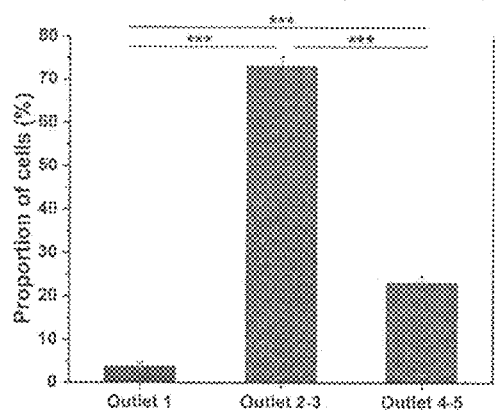
FIG. 7B is a graph showing normalized CFU data for a high-level infection.

FIG. 7B is a graph showing the proportion of cells in various outlets of the microfluidic device in FIG. 1A for a high-level infection. The normalized CFU data in each outlet is shown for whole blood samples spiked with infected monocytes.

Figure 7C:
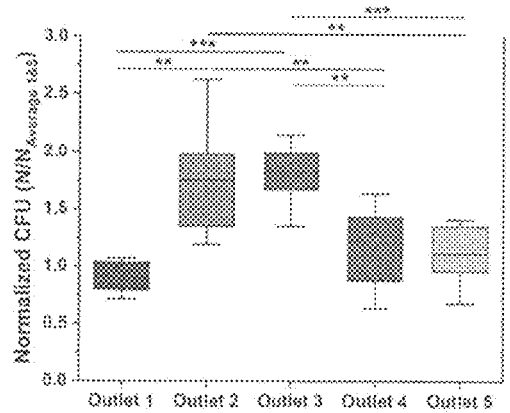
FIG. 7C is a graph showing CFU data normalized to the average CFU level of outlet 1 and 5 for a low-level infection.

FIG. 7C is a graph showing CFU data normalized to the average CFU level of outlet 1 and 5 for a low-level infection.

Figure 7D:
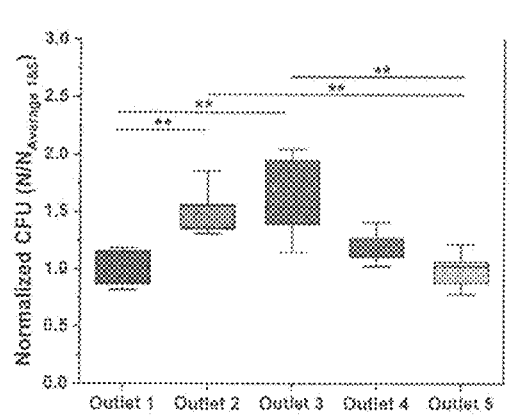
FIG. 7D is a graph showing CFU data normalized to the average CFU level of outlet 1 and 5 for a high-level infection.

FIG. 7D is a graph showing CFU data normalized to the average CFU level of outlet 1 and 5 for a high-level infection.

Figure 8:
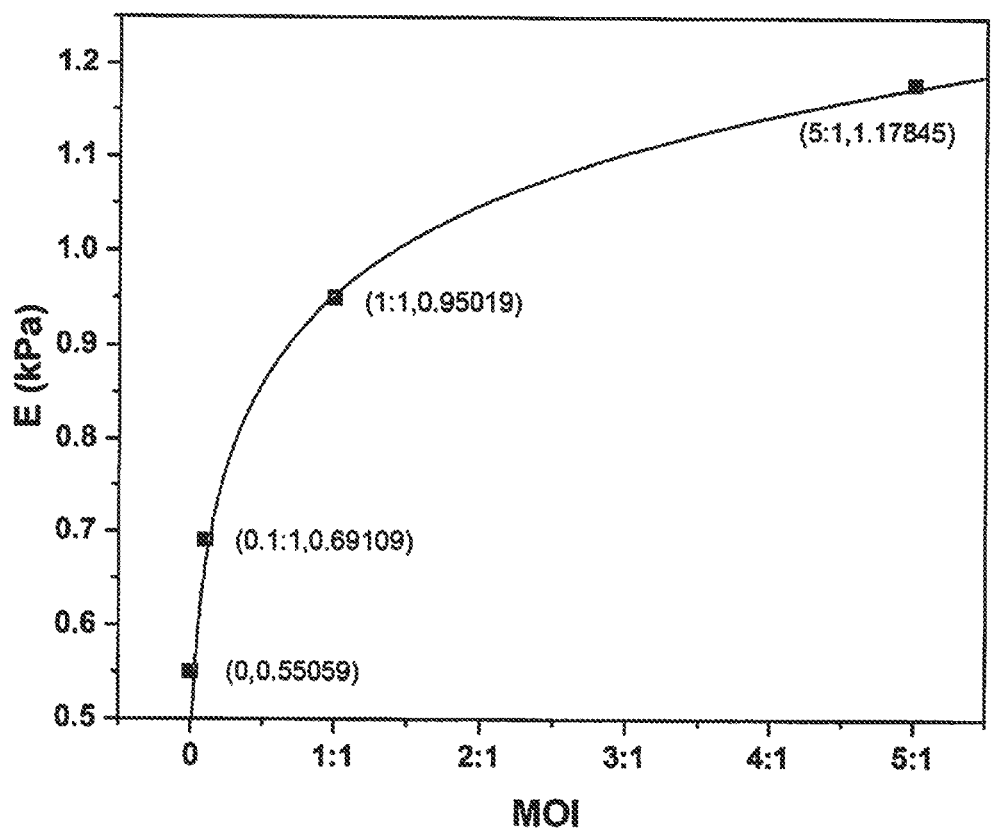
FIG. 8 shows a graph correlating MOIs and stiffness (E)

FIG. 8 shows a graph correlating MOIs and stiffness (E). The data points for this tight, positive correlation were obtained with uninfected sample (0, 0.55059), sample infected at lower MOI (<0.1:1) (0.1, 0.69109), middle MOI (<1:1) (1, 0.95019) and higher MOI (<5:1) (5, 1.17845).

FIGS. 9A-9D show the outlet distribution of MIMs infected with P. aeruginosa. In FIGS. 9A-9D, outlet 1=outlet 24a in FIG. 1A, outlet 2=outlet 24b, outlet 3=outlet 24c in FIG. 1A, outlet 4=outlet 24d in FIG. 1A, and outlet 5=outlet 24e in FIG. 1A. In FIG. 9, * states for p values of <0.01,  states for p values of <0.001, * states for p values of <0.0001.

FIG. 9A shows the outlet distribution of MIMs infected with P. aeruginosa for MOI<0.1:1 where a large proportion (>90%) of MIMs are sorted to outlets 2 and 3 (outlets 24b and 24c in FIG. 1A, respectively).

FIG. 9B shows the outlet distribution of MIMs infected with P. aeruginosa for MOI<1:1 where a large proportion (>95%) of MIMs are sorted to outlets 2 and 3 (outlets 24b and 24c in FIG. 1A, respectively).

FIG. 9C shows the distribution in various outlets of MIMs infected with P. aeruginosa at MOI<0.1:1. This figure shows that outlets 2 and 3 (outlets 24b and 24c in FIG. 1A, respectively) provide significantly higher MIMs about 1.5-1.6x of CFUs normalized to the average CFUs of outlets 1 and 5.

FIG. 9D shows the distribution in various outlets of MIMs infected with *P. aeruginosa* at MOI<1:1. This figure shows that outlets 2 and 3 (outlets 24*b* and 24*c* in FIG. 1A, respectively) provide significantly higher MIMs about 1.6-1.7× of CFUs normalized to the average CFUs of outlets 1 and 5.

Figure 10:
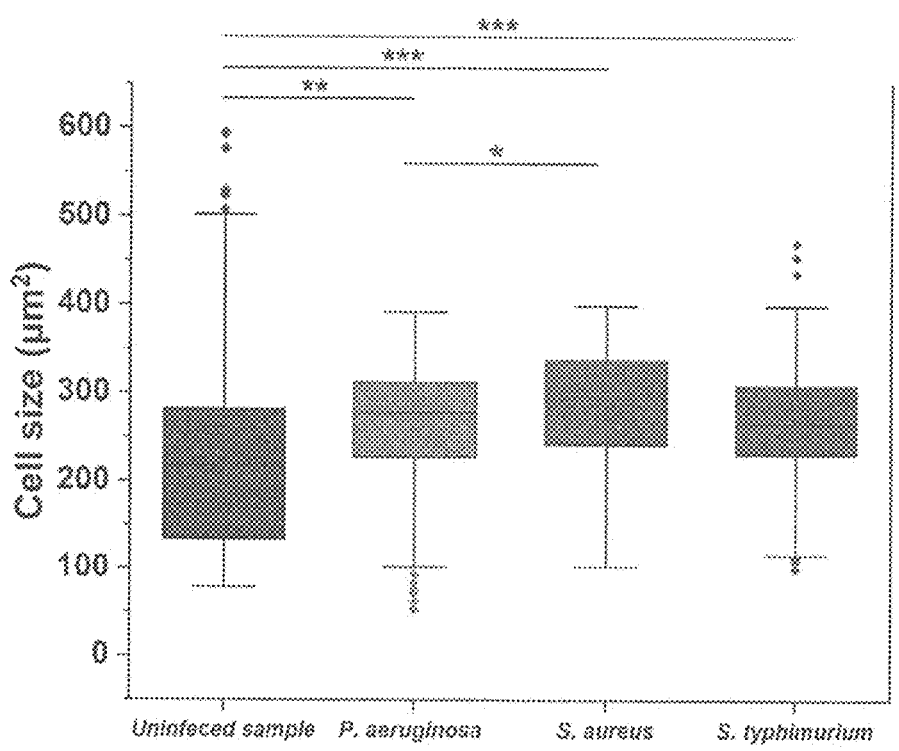
FIG. 10 shows relative sizes of uninfected monocytes and various MIMs.

Similar results to FIGS. 9A-9D are seen with *S. aureus, S. typhimurium, S. agalactiae* and *K. pneumoniae*, whether the bacteria is living or dead FIG. 10 shows relative sizes of uninfected monocytes (less than 250 μm$^2$) and various MIMs such as *P. aeruginosa* (about 275 μm$^2$), *S. aureus* (about 290 μm$^2$), and *S. typhimurium* (about 265 μm$^2$), showing that the MIMs are significantly larger than uninfected monocytes. In FIG. 10, * states for p values of <0.01,  states for p values of <0.001, * states for p values of <0.0001.

FIG. 11A shows the proportion of cells for various outlets for neutrophil-rich samples infected with *P. aeruginosa* at a MOI<0.1:1, where over 70% are sorted into outlets 2 and 3.

FIG. 11B shows the proportion of cells for various outlets for neutrophil-rich samples infected with *P. aeruginosa* at a MOI<1:1 where about 75% are sorted into outlets 2 and 3.

In FIGS. 11A-11B, outlet 1=outlet 24*a* in FIG. 1A, outlet 2=outlet 24*b*, outlet 3=outlet 24*c* in FIG. 1A, outlet 4=outlet 24*d* in FIG. 1A, and outlet 5=outlet 24*e* in FIG. 1A. In FIG. 9, * states for p values of <0.01,  states for p values of <0.001, * states for p values of <0.0001.

Figure 12A:
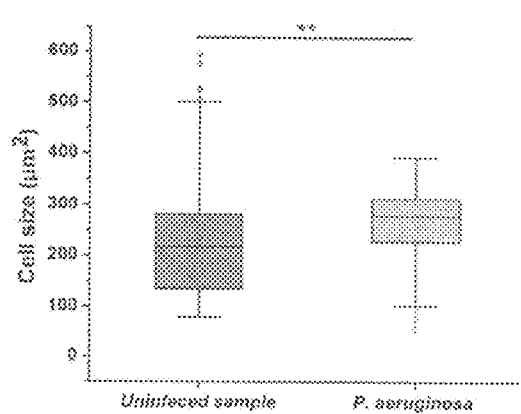
FIG. 12A shows an analysis of the cell size of MIPs as compared to uninfected monocytes and indicates that MIPs infected with *P. aeruginosa*.

FIG. 12A shows an analysis of the cell size of MIPs as compared to uninfected monocytes and indicates that MIPs infected with *P. aeruginosa* are over about 250 μm$^2$ while uninfected monocytes are about 200 μm$^2$. Thus, it is clear that infected monocytes are significantly larger than uninfected monocytes which likely contributes to the differential cell focusing within the microfluidic device's microchannel. However, the size of most infected monocytes (MOI of about 50:1; bacteria: cancer cell) still overlaps considerably with that of uninfected monocytes, indicating other factors are also in play, mediating the efficient focusing and separation of infected monocytes.

Figure 12B:
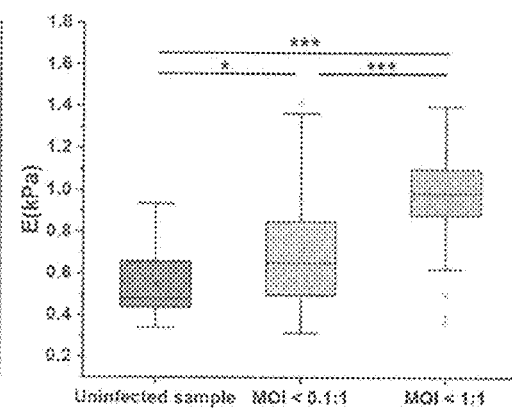
FIG. 12B is a graph showing the stiffness of MOIs and uninfected monocytes.

FIG. 12B is a graph showing the stiffness of MOIs and uninfected monocytes (Uninfected: 0.55±0.03 kPa; MOI<0.1:1: 0.69±0.04 kPa; MOI<1:1: 0.95±0.24 kPa), at a pressure of 0.1 kPa.

In FIGS. 12A and 12B, * states for p values of <0.01,  states for p values of <0.001, * states for p values of <0.0001.

Figure 12C:
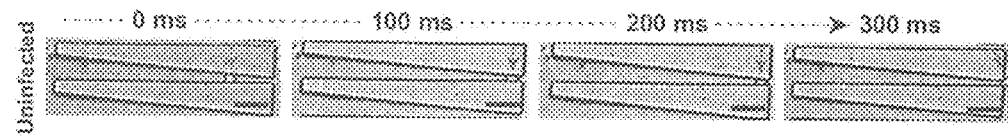
FIG. 12C shows representative time-lapse freeze frames of uninfected monocytes (indicated with the arrow) passing through the stiffness evaluation device.

FIG. 12C shows representative time-lapse freeze frames of uninfected monocytes (indicated with the arrow) passing through the stiffness evaluation device.

Figure 12D:
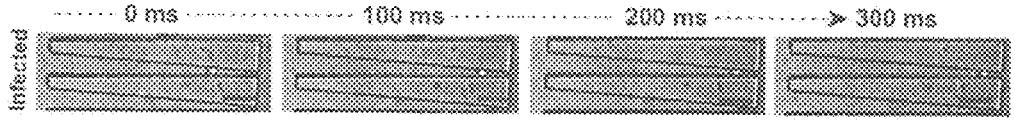
FIG. 12D shows representative time-lapse freeze frames of MIMs (indicated with the arrow) passing through the stiffness evaluation device The figures herein are for illustrative purposes only and are not necessarily drawn to scale.

In contrast, FIG. 12D shows representative time-lapse freeze frames of MIMs (indicated with the arrow) passing through the stiffness evaluation device.

Accordingly, as the MIM proceeds more slowly through the stiffness evaluation device, it is understood that the MIM of FIG. 12D is more stiff than the uninfected monocyte of FIG. 12C.

In FIGS. 12C and 12D, the scale bar=50 μm and ms=millisecond.

Accordingly, an embodiment of the present invention relates to a method for diagnosing asymptomatic cases or infections presenting mild symptoms caused by low levels of a microbe; or a pathogen; or a bacteria, in the early stage or recurrence of pathogen infection. In contrast, the microfluidic device used only optical imaging to generate outputs reflecting the presence of infection, and the analysis could be rapidly established within 1.5 h. With the ease of operations and low cost of fabrication, clinicians can screen samples efficiently to identify samples from patients at a potential risk of infection, facilitating early treatment interventions.

An embodiment of the invention herein relates to a method for detecting an infected cell; or an MIM, in a fluid sample comprising the steps of providing a microfluidic device, introducing the fluid sample into the inlet at a predetermined flow rate, collecting the output from an outlet, and quantifying the amount of infected cells in the output.

TABLE 1

Comparison of microfluidic device compared with other existing technologies.

| | Type | Pathogen-type | Time | Cost | Mode of detection |
|---|---|---|---|---|---|
| Culture-based | Blood culture | Bacteria | >2 days | Low | Planktonic bacteria |
| Gene-based | Karius test (cfDNA based) | Bacteria, virus, fungus, etc. | 24 h-96 h | High | Genes |
| | Aptamer-Based Recognition | *S. aureus* and *Escherichia coli* | <2 h | Med. | Planktonic bacteria |
| | Immunoaffinity mass spectrometry | *Escherichia coli, Bacillus subtilis,* and *S. aureus* | 12 h | High | Planktonic bacteria |
| Protein-based | Enzyme-based immunodetection assay | SARS-CoV-2 | >24 h (MOI ≥ 3:1); >48 h (MOI 1:200) | Med. | Enzymes |
| | Integrated Comprehensive Droplet Digital Detection system | *Escherichia coli* | 1.5-4 h | High | Enzymes |
| Physical property-based | MIM Biosensor for phagocytosis detection | *P. aeruginosa, S. aureus, S. typhimurium, S. agalactiae, K. pneumoniae* and patient derived clinical isolates | <1.5 h (MOI > 0.01:1) | Low | Intracellular bacteria |

Current microbial infection detection methods such as those in Table 1 may rely upon, for example, antibody tests or culture tests for blood stream and urinary tract infections. However such systems and methods are based upon detecting the free-floating microbes, which may only be detectable when there is a high microbial concentration in the fluid. The antibody-based assays require labeled antibodies, such as monoclonal antibodies grown in mice, which require time and expertise to produce and prepare.

In contrast, it is believed that the present inertial focusing method, system, and device herein provides a label-free assay which separates based on physical cell properties between, for example, uninfected monocytes and MIMs. Such embodiments are more ecofriendly, easier, and require less preparation than traditional antibody-based methods. The affordable and flexible methods herein are therefore useful when encountering with very early-stage infections, and/or detection of microbes; or new microbes, which have not yet been characterized, whose DNA has not yet been sequenced, to which monoclonal antibodies have not yet been raised, etc.

It is therefore believed that the microfluidic device herein may therefore detect bloodstream infections as MIMs are stiffer and larger than uninfected monocytes. The device is able to derive a threshold of 7.1% for the proportion of cells in target outlets reflecting $P.$ $aeruginosa$ infections and to further identify low-dose infections between a MOI of from about 0.1:1 to about 1:1 using a threshold of 4.95%. Furthermore, the microfluidic device's optimal cell concentration corresponded to the use of only a small volume of blood samples (~ 1 ml), thus facilitating routine and point-of-care detection, as well as reducing potential pain for patients as only a small amount of bodily fluid, or blood, is required.

The collecting step in the method herein may further include collecting the output from each outlet to comprise a plurality of outputs, and wherein the quantifying step comprises quantifying the amount of infected cells in each of the plurality of outputs.

It is recognized that the method herein may seek to test and/or separate cells from various fluids, such as bodily fluids, and therefor in an embodiment herein, the fluid includes comprises a body fluid selected from the group of blood, urine, sputum, lymph fluid, spinal fluid, semen, a tissue extract, and a combination thereof; or sputum, blood and a combination thereof; or saliva; or blood. Where the fluid sample is or contains a blood sample, the method may further include the step of pre-treating the blood sample to lyse the red blood cells prior to introducing the fluid sample into the inlet.

In an embodiment herein, the fluid sample may contain an immune cell; or a myeloid cell, a lymphoid cell, and a combination thereof; or a phagocyte, a T cell, a B cell, a natural killer cell, and a combination thereof; or a monocyte, a neutrophil, and a combination thereof; or a monocyte; or a neutrophil, at a concentration of from about 0 cells/ml to about $10 \times 10^6$ cells/ml; or from about $1 \times 10^3$ cells/ml to about $1 \times 10^6$ cells/ml.

In an embodiment herein, the infected cell is a phagocyte, such as a monocyte, a neutrophil, and a combination thereof; or a monocyte; or a neutrophil. Further, the phagocyte may bind to or contain at least one microbe; or a pathogen. The microbe may be selected from the group of a bacteria, a fungi, an amoeba, a protozoa, a virus, and a combination thereof; or may be a Gram-negative bacteria.

In addition to the detection of Gram-negative bacterial infections, the microfluidic device herein may also be adapted to detect other phagocytosed microbes, via, for example, processing clinical samples at various serial dilutions within the optimal cell concentration range (about $0.1 \times 10^6$ cells per ml to about $1 \times 10^6$ cells per ml) to recalibrate the threshold of negative results. Furthermore, the microfluidic device may be suitably used to detect infections caused by intracellular microbes; or bacteria, hiding within host cells, as these microbes would otherwise evade the immune system. It is believed that the microfluidic device herein may also be widely applied to provide point of care (POC) systems for patients with pathogenic infections such as, for example, fungi and virus.

Materials and Methods $P.$ $aeruginosa$ and Monocyte Cell Cultures $P.$ $aeruginosa$ is cultured in 2 ml Luria-Bertani (LB) media (Becton, Dickinson and Company, #244620, USA) at 37° C. overnight, where bacteria concentrations reach approximately $10^9$ cells/ml. Bacteria suspensions are centrifuged at 10,000 rpm for 3 min and re-suspended in 1 ml PBS. To visualize the infection of bacteria, $P.$ $aeruginosa$ is transformed with Tn7-gfp plasmid for expression of green fluorescent protein (GFP).

Human myeloid leukemia cell line (U937) is maintained in RPMI-1640 (Gibco, #11875085, USA) and supplemented with 10% FBS (Gibco, #10270106, USA) and 1% penicillin-streptomycin (Gibco, #15140122, USA). Cells are cultured in optimal conditions under 5% $CO_2$ atmosphere at 37° C. under humidified conditions. Media are refreshed every 48 h, and cells are passaged at 80% confluence.

Infection Assay

For the infection test, monocytes are washed three times with phosphate buffer saline (PBS) (Gibco, #70011044, USA) and transferred to fresh RPMI-1640 medium+10% PBS. Cells are infected with $P.$ $aeruginosa$ at different MOIs (10:1, 1:1, and 1:10) and incubated at 37° C. under 5% $CO_2$ for 2 h. Infected samples are centrifuged at 1500 rpm for 5 min and re-suspended in fresh cell culture media three times to remove unbound extracellular bacteria.

Device Processing

Bonded devices are assessed for leakages before use. Samples are re-suspended in 1.5 ml PBS and introduced to the microfluidic device at a flow rate of 1.7 ml/min, using a syringe pump (New Era Pump System, Inc., Farmingdale, New York, USA).

Cell Viability and Immunostaining

Monocytes are stained with 5 µM nuclear dye Hoechst (blue), Calcein AM (Invitrogen, #C3100MP, USA) and 5 µM Propidium Iodide (PI) (Sigma-Aldrich, #81845, USA) respectively, and incubated under 37° C. for 30 min (Calcein AM), room temperature for 1 min (PI) to identify live and dead cells. Samples are washed with PBS prior to fluorescence imaging with a fluorescence microscope (Nikon, Eclipse Ci-L, Japan).

Stiffness Measurement

Monocytes are injected into the device for stiffness measurement as described herein, under a pressure of 0.1 kPa using a pump, and the deformability of monocytes is obtained. Briefly, the device for stiffness measurement is fabricated by soft lithography based on PDMS. Before the test is conducted, the device is coated with 1% (w/w) pluronic F-127 (Sigma-Aldrich, P2443, USA) for 30 min to prevent cell adhesion. A phase-contrast inverted microscope (Nikon, Eclipse Ci-L, Japan) is used to capture monocytes' images under 100 Pa pressure.

Colony-Forming Unit (CFU) Assay

Bacterial suspensions are collected and serially diluted for growth on an LB agar plate (Sigma-Aldrich, #L3027, USA) at 37° C. for 24 h to quantify bacterial counts. CFU/ml is tabulated by the average number of colonies×dilution factor×volume. For CFU data at MOI<1:1, and the data is normalized by dividing the average CFU value of outlet 1 (e.g., outlet 24a in FIG. 1A) and 5 (e.g., outlet 24e of FIG. 1A).

Control Assays with Activated Monocytes

Activated monocytes are obtained by treating naive monocytes with 0.22-μm filter-sterilized LB media conditioned with live bacteria for 2 h or exposure to heat-killed bacteria (MOI 10:1).

Imaging and Analysis

Cell suspensions are collected from each outlet for imaging under a fluorescent microscope. The nuclei of cells are stained by 5 μM Hoechst (Invitrogen, #H1399, USA) to quantify recovery and cell proportions. Images of monocytes with and without internalized pathogens are obtained to compare the sizes before and after bacterial infection, and the cell size is analyzed with predetermined algorithms. All fluorescent images are processed by Image J software (National Institutes of Health, USA). Automated algorithms are used to establish cell counts and quantify intensity outputs. Fluorescent intensity is normalized to background intensity values. Data are plotted by Origin software (OriginLab Corporation, USA). Thus, in an embodiment herein, the quantifying step may include an optical imaging step.

Statistical Analysis

The results are expressed as means±standard deviation. Data groups are compared using the one-way ANOVA and Student's t-test to evaluate associations between independent variables, and the P values are obtained. Three independent trials are conducted in triplicates for each experiment.

It should be understood that the above only illustrates and describes examples whereby the present invention may be carried out, and that modifications and/or alterations may be made thereto without departing from the spirit of the invention.

It should also be understood that certain features of the invention, which are, for clarity, described in the context of separate embodiments, may also be provided in combination in a single embodiment. Conversely, various features of the invention which are, for brevity, described in the context of a single embodiment, may also be provided separately, or in any suitable subcombination.

All references specifically cited herein are hereby incorporated by reference in their entireties. However, the citation or incorporation of such a reference is not necessarily an admission as to its appropriateness, citability, and/or availability as prior art to/against the present invention.

The invention claimed is:

1. A method for detecting an immune cell comprising an internalized microbe in a fluid sample comprising the steps of:
    A. providing a microfluidic device comprising:
        i. an inlet to receive a fluid sample with an immune cell with an internalized microbe and an immune cell without an internalized microbe;
        ii. a curvilinear microchannel in fluid communication with the inlet, the curvilinear microchannel is configured in a loop concentrically surrounding the inlet, wherein at least a curve portion of the loop has a rectangular cross-section along a substantial portion of the length of the curved portion enabling the detection of the immune cell with an internalized microbe from the immune cell without an internalized microbe in the fluid sample through their differences in cell deformability, wherein the microchannel has an inner wall; and
        iii. a plurality of outlets in fluid connection with the curvilinear microchannel, wherein at least two of the outlets closest to the inner wall of the microchannel receive the immune cell with an internalized microbe; each of the outlets receive the immune cell without an internalized microbe,
    wherein the plurality of outlets is from about 2 outlets to about 20 outlets;
    B. introducing the fluid sample into the inlet at a predetermined flow rate of from about 1.3 ml/min to about 2.1 ml/min; or from about 1.5 ml/min to about 1.9 ml/min; or about 1.7 ml/min;
    C. individually collecting the output from the plurality of outlets; and
    D. quantifying a proportion of the immune cells with an internalized microbe in each of the outputs, thereby enabling determination of infection stage of the fluid sample;
        wherein the quantifying step comprises an optical imaging step.

2. The method according to claim 1, wherein the inlet consists essentially of one inlet and the plurality of outlets comprise from about 2 outlets to about 15 outlets; or from about 3 outlets to about 10 outlets; or wherein the plurality of outlets consists of 5 outlets.

3. The method according to claim 1, wherein the curvilinear microchannel branches to form the plurality of outlets.

4. The method according to claim 3, wherein the distance between the adjacent outlets is from about 100 μm to about 500 μm; or from about 150 μm to about 450 μm; or from about 200 μm to about 400 μm; or from about 250 μm to about 350 μm; or about 250 μm.

5. The method according to claim 1, wherein the curvilinear microchannel has a width of from about 200 μm to about 800 μm; or from about 300 μm to 700 μm; or from about 400 μm to about 650 μm; or from about 450 μm to about 550 μm.

6. The method according to claim 1, wherein the curvilinear microchannel has a height of from about 50 μm to about 350 μm; or from about 80 μm to about 325 μm; or from about 100 μm to about 310 μm; or from about 130 μm to about 275 μm; or from about 150 μm to about 250 μm, as measured horizontally between the inner and outer walls of the channel.

7. The method according to claim 1, wherein at least a portion of the microfluidic device produced by a method comprising lithography, 3D printing, and a combination thereof.

8. The method according to claim 1, wherein the individually collecting step comprises collecting the output from each outlet to comprise a plurality of outputs, and wherein the quantifying step comprises quantifying the proportion of the immune cell with an internalized microbe in each of the plurality of outputs.

9. The method according to claim 1, wherein the fluid sample comprises a body fluid selected from the group consisting essentially of blood, urine, sputum, lymph fluid, spinal fluid, semen, a tissue extract, and a combination thereof.

10. The method according to claim 1, wherein the immune cell comprises a myeloid cell, a lymphoid cell, and a combination thereof; or a phagocyte, a T cell, a B cell, a natural killer cell, and a combination thereof; or a monocyte, a neutrophil, and a combination thereof; or a monocyte; or a neutrophil.

11. The method according to claim 10, wherein the immune cell binds to or contains at least one microbe; or a pathogen, a parasite and a combination thereof; or wherein the microbe is selected from the group consisting essentially of a bacterium, a fungi, a virus, a parasite, an amoeba, a protozoa, a virus, and a combination thereof; or wherein the microbe is a Gram-negative bacteria.

12. The method according to claim 1, wherein the fluid sample is a blood sample and wherein the method further comprises the step of pre-treating the blood sample to lyse the red blood cells prior to introducing the fluid sample into the inlet.

13. The method according to claim 1, wherein the fluid sample comprises an immune cell at a concentration of from about 0 cells/ml to about $10 \times 10^6$ cells/ml; or from about $1 \times 10^3$ cells/ml to about $1 \times 10^6$ cells/ml.

14. The method according to claim 1, wherein the microbe is selected from the group consisting of bacterium, a fungi, a virus, a parasite, an amoeba, a protozoa, a yeast, and a combination thereof.

* * * * *